United States Patent
Cancio et al.

(10) Patent No.: US 6,514,208 B1
(45) Date of Patent: Feb. 4, 2003

(54) METHOD AND APPARATUS FOR POWER DOPPLER ULTRASOUND IMAGE ANALYSIS

(75) Inventors: Leopoldo C. Cancio, San Antonio, TX (US); Natalia P. Matylevitch, San Antoino, TX (US); Toshiyuki Kuwa, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/534,328

(22) Filed: Mar. 24, 2000

Related U.S. Application Data

(60) Provisional application No. 60/159,647, filed on Oct. 18, 1999, provisional application No. 60/160,204, filed on Oct. 19, 1999, and provisional application No. 60/160,635, filed on Oct. 20, 1999.

(51) Int. Cl.[7] ................................................. A61B 8/00
(52) U.S. Cl. ..................... 600/454; 600/443; 600/455
(58) Field of Search ................................ 600/440, 458, 600/447, 454, 455, 443, 444, 449

(56) References Cited

U.S. PATENT DOCUMENTS

| | | | |
|---|---|---|---|
| 4,998,553 A | | 3/1991 | Winkelman |
| 5,575,289 A | | 11/1996 | Skidmore ............. 128/661.08 |
| 5,855,556 A | * | 1/1999 | Shirai ......................... 600/440 |
| 5,983,120 A | | 11/1999 | Groner et al. |
| 6,123,670 A | * | 9/2000 | Mo ............................ 600/447 |
| 6,162,176 A | * | 12/2000 | Washburn et al. .......... 600/454 |
| 6,258,033 B1 | * | 7/2001 | Greneon ..................... 600/458 |

OTHER PUBLICATIONS

Argenta, et al., "Vacuum–Assisted Closure: A New Method for Wound Control and Treatment: Clinical Experience," Annals of Plastic Surgery, Jun. 1997, vol. 38, No. 6, pp. 563–576.

Shung, et al., "Scattering of Ultrasound by Blood," IEEE Transactions on Bio–medical Engineering, Nov. 1976, vol. BME–23, No. 6, pp. 460–467.

Kasai et al., "Real–Time Two–Dimensional Blood Flow Imaging Using an Autocorrelation Technique," IEEE Transactions on Sonics and Ultrasonics, May 1985, vol. SU–32, No. 3, pp. 458–464.

Akiyama, et al., "Hemodynamic Study of Renal Transplant Chronic Rejection Using Power Doppler Sonography," Transplant Proceedings, Jun. 1996, vol. 28, No. 3, pp. 1458–1460.

"Manual for Using Fluorescent Microspheres to Measure Regional Organ Profusion," Division of Pulmonary and Critical Medicine, University of Washington, Apr. 1995, pp. 1–37.

Austin et al., "Determination of Regional Myocardial Blood Flow Using Fluorescent Microspheres," American Journal of Cardiovascular Pathology, 1993, vol. 4, No. 4, pp. 352–357.

(List continued on next page.)

Primary Examiner—Francis J. Jaworski
Assistant Examiner—Maulin Patel
(74) Attorney, Agent, or Firm—Elizabeth Arwine

(57) ABSTRACT

This invention relates to estimating the amount of blood flowing to the tissues of the kidney. More particularly, the invention is related to analyzing obtained power Doppler ultrasound images taken of the kidney and even more specifically of the kidney cortex tissue to produce a numerical value that correlates to the blood flow.

20 Claims, 26 Drawing Sheets

OTHER PUBLICATIONS

Breidahl et al., "Power Doppler Sonography in the Assessment of Musculoskeletal Fluid Collections," American Journal of Roentgenology, 1996, vol. 166, No. 3, pp. 1443–1446.
Bude et al., "Power Versus Conventional Color Doppler Sonography: Comparison in the Depiction of Normal Intrarenal Vasculature," Gentourinary Radiology, Sep. 1994, vol. 192, No. 3, pp. 777–780.
Carter et al., "Hepatic and Intestinal Blood Flow Following Thermal Injury," Journal of Burn Care & Rehabilitation, Jul./Aug. 1998, vol. 9, No. 4, pp. 347–350.
Carter et al., "Intrarenal Redistribution of Blood Flow in the Early Postburn Period," Journal of Trauma, Oct. 1975, vol. 15, No. 10, pp. 877–876.
Chen et al., "Color and Power Doppler Imaging of the Kidneys," World Journal of Urology, 1998, vol. 16, pp. 41–45.
Cioffi et al., "Cause of Mortality in Thermally Injured Patients," Steinkopff Verlag Darmstadt, 1993, pp. 7–11.
Clautice–Engle et al., "Renal Hypoperfusion: Value of Power Doppler Imaging," American Journal of Roentgenology, May 1997, vol. 168, pp. 1227–1231.
Clautice–Engle et al., "Power Doppler Imaging of Focal Lesions of the Gastrointestinal Tract: Comparison with Conventional Color Doppler Imaging," Journal of Ultrasound Medicine, 1996, vol. 15, pp. 63–66.
Dacher et al., "Power Doppler Sonographic Pattern of Acute Pyelonephritis in Children: Comparison with CT," American Journal of Roentgenology, Jun. 1996, vol. 166, pp. 1451–1455.
Dries et al., "Adequate Resuscitation of Burn Patients may not be Measured by Urine Output and Vital Signs," Critical Care Medicine, Mar. 1991, vol. 19, No. 3, pp. 327–329.
Durick et al., "Renal Perfusion: Pharmacologic Changes Depicted with Power Doppler US in an Animal Model," Radiology, Dec. 1995, vol. 197, No. 3, pp. 615–617.
Dymling et al., "Measurement of Blood Perfusion in Tissue Using Doppler Ultrasound," Ultrasound in Medicine and Biology, 1991, vol. 17, No. 5, pp. 433–444
Glenny et al., "Validation of Fluorescent–labeled Microspheres for Measurement of Regional Organ Perfusion," Journal of Applied Physiology, 1993, vol. 74, pp. 2585–2597.
Griewing et al., "Cerebrovascular Disease Assessed by Color–Flow and Power Doppler Ultrasonography," Stroke, Jan. 1996, vol. 27, No. 1, pp. 95–100.
Hélénon et al., "Renal Vascular Doppler Imaging: Clinical Benefits of Power Mode," Radiographics, Nov.–Dec. 1998, vol. 18, pp. 1441–1457.
Karlberg et al., "Impaired Medullary Circulation in Postischemic Acute Renal Failure," Acta Physiologica Scandinavica, 1983, vol. 118, pp. 11–17.
Kirkebø et al., "Blood Flow Heterogeneity in the Renal Cortex During Burn Shock in Dogs," Acta Physiologica Scandinavica, 1985, vol. 123, pp. 205–213.
Luker et al., "Scrotal US in Pediatric Patients: Comparison of Power and Standard Color Doppler US," Radiology, Feb. 1996, vol. 198, No. 2, pp. 381–385.
Martinoli et al., "Interlobular Vasculature in Renal Transplants: A Power Doppler US Study with MR Correlation," Radiology, Jul. 1996, vol. 200, No. 1, pp. 111–117.
Martinoli et al., "Power Doppler Sonography: Clinical Applications," European Journal of Radiology, 1998, vol. 27, pp. S133–S140.

Mason et al., "Disparity Between Surface and Deep Nephron Function Early After Renal Ischemia," Kidney International, 1983, vol. 24, pp. 27–36.
Miller et al., "Effect of Warm Ischemic Damage on Intrarenal Distribution of Flow in Preserved Kidneys," Surgery, Aug. 1972, vol. 72, No. 2, pp. 193–202.
Newman et al., "Detection of Soft–Tissue Hypermia: Value of Power Doppler Sonography," American Journal of Roentgenology, Aug. 1994, vol. 163, pp. 385–389.
Newman et al., "Power Doppler Sonography of Synovitis: Assessment of Therapeutic Response–Preliminary Observations," Radiology, Feb. 1996, vol. 198, pp. 582–584.
Nielsen et al., "Some Comparative Aspects of Porcine Renal Function," Swine in Biomedical Research, 1965, pp. 529–536.
Parro et al., "Amplitude Information From Power Doppler Color Flow Mapping Systems: A Preliminary Study of the Power Mode," Journal of American College of Cardiology, Oct. 1991, vol. 18, No. 4, pp. 997–1003.
Rector et al., "Effect of Hemorrhage and Vasopressor Agents on Distribution of Renal Blood Flow," American Journal of Physiology, May 1972, vol. 222, No. 5, pp. 1125–1131.
Rozycki et al., "Surgeon–Performed Ultrasound: Its Use in Clinical Practice," Annals of Surgery, 1998, vol. 228, No. 1, pp. 16–28.
Rubin et al., "Power Doppler US: A Potentially Useful Alternative to Mean Frequency–based Color Doppler US," Radiology, 1994, vol. 190, No. 3, pp. 853–856.
Sevitt et al., "Burns: Pathology and Therapeutic Applications," London: Butterworth & Co., 1957, pp. 18–27.
Shanser et al., "The Effect of Decreased Renal Artery Perfusion Pressure on Interenal Hemodynamics in the Dog," Investigative Radiology, Nov./Dec. 1975, vol. 10, pp. 569–582.
Stein et al., "Mechanisms of the Redistribution of Renal Cortical Blood Flow During Hemorrhagic Hypotension in the Dog," Journal of Clinical Investigation, 1973, vol. 52, pp. 39–47.
Steinke et al., "Sonographic Assessment of Carotid Artery Stenosis," Stroke, Jan. 1996, vol. 27, No. 1, pp. 91–93.
Tasaki et al., "Effects of Burns on Inhalation Injury," Journal of Trauma, Oct. 1997, vol. 43, No. 4, pp. 603–607.
Taylor et al., "Renal Cortical Ischemia in Rabbits Revealed by Contrast–Enhanced Power Doppler Sonography," American Journal of Roentgenology, Feb. 1998, vol. 170, pp. 417–422.
Tranquilli et al., "Organ Blood Flow and Distribution of Cardiac Output in Nonanesthetized Swine," American Journal of Veterinary Research, May 1982, vol. 43, No. 5, pp. 895–897.
Tureschek et al., "Power Doppler Versus Color Doppler Imaging in Renal Allograft Evaluation," Journal of Ultrasound in Medicine, 1996, vol. 15, pp. 517–522.
William D. Winters, "Power Doppler Sonographic Evaluation of Acute Pyelonephritis in Children," Journal of Ultrasound in Medicine, 1996, vol. 15, pp. 91–98.
Kuwa et al., "Evaluation of Renal Cortical Perfusion by Non–Invasive Power Doppler Ultrasonography During Burn Shock," Journal of Burn Care and Rehabilitation, Jan./Feb. 1999, vol. 20, No. 1, Part 2, p. S139.
Kuwa et al., "Evaluation of Renal Cortical Perfusion by Non–Invasive Power Doppler Ultrasonography During Burn Shock," paper presented at $31^{st}$ Annual Meeting of American Burn Association, Mar. $24^{th}$–$25^{th}$, 1999.

Morgan et al., "Water Metabolism and Antidiuretic Hormone (ADH) Response Following Thermal Injury," Journal of Trauma, 1980, vol. 20, No. 6, pp. 468–472.

Stein et al., "Alterations in Intrarenal Blood Flow Distribution," Circulation Research, May 1973, vol. 32, pp. I61–I72.

Kuwa et al., "Evaluation of Renal Cortical Perfusion by Non–Invasive Power Doppler Ultrasonography During Burn Shock," PowerPoint presentation with notes from the $31^{st}$ Annual Meeting of American Burn Association, Mar. $24^{th}$–$25^{th}$, 1999.

Newhouse et al., "Invariance of the Doppler Bandwidth with Flow Displacement in the Illuminating Field," Journal of the Acoustical Society of America, Nov. 1991, vol. 90, No. 5, pp. 2595–2601.

S. Ritter, "Doppler Color Flow Mapping 1989: Industry Speaks," Echocardiography, 1989, vol. 6, No. 5, pp. 467–469.

* cited by examiner

METHOD AND APPARATUS FOR POWER DOPPLER ULTRASOUND IMAGE ANALYSIS

This application claims priority from U.S. provisional Application Ser. No. 60/159,647, filed Oct. 18, 1999, U.S. provisional Application Ser. No. 60/160,204, filed Oct. 19, 1999, and U.S. provisional Application Ser. No. 60/160,635, filed Oct. 20, 1999.

I. FIELD OF THE INVENTION

This invention relates to estimating the amount of blood flowing to the tissues of the kidney. More particularly, the invention is related to analyzing obtained power Doppler ultrasound images taken of the kidney and even more specifically of the kidney cortex tissue to produce a numerical value that correlates to the blood flow.

II. BACKGROUND OF THE INVENTION

Patients suffering from shock have impaired blood flow to the vital organs. The kidney is one such organ. A goal of therapy is to restore blood flow to these organs, including the kidney and in particular the cortex thereof.

Pulmonary artery catheters are often placed during complicated resuscitations, but they carry finite risks such as pneumothorax, pulmonary artery laceration, pulmonary infarction, and line sepsis. Also, data derived from pulmonary artery catheters, arterial blood gases, and so forth address global perfusion but not regional organ perfusion, whereas the latter may be more important in resuscitation.

Shock may result from a burn. Most thermally injured patients respond to standard resuscitation regimens, in which a physiologic crystalloid solution is infused at a rate dictated by total burn surface area and weight, with titration of that rate based primarily on the adequacy of the urine output. However, this approach fails on occasion, particularly in massively burned patients. A recent review at the U.S. Army Institute of Surgical Research Burn Center revealed that 12 of 93 nonsurviving burn patients (13 percent) were resuscitation failures, in whom hemodynamic stability could not be achieved as discussed by Cioffi et al. in "Cause Of Mortality in Thermally Injured Patients," *Die Infektion beim Brandverletzten: Proceedings of the "Infektionsprophylaxe und Infektionshekampfung beim Brandverletzten" International Symposium*, ed. S. Lorenz & P.-R. Zellner, Darmstadt: Steinkopff Verlag, 1993, pp. 7–11. To salvage these high risk patients, new monitoring devices that accurately assess tissue perfusion may be necessary.

Furthermore, in patients with acute renal failure—whether oliguric or non-oliguric—urine output does not necessarily reflect renal perfusion. This is likewise true of patients who have received a diuretic, whose urine output is driven by glycosuria or nitrogen metabolites, or those in whom alcohol has inhibited antidiuretic hormone. Also, an intervention intended to improve renal blood flow, such as the institution of an inotropic agent or a bolus of an intravenous crystalloid solution, may affect urine output in delayed fashion. Clinicians frequently estimate kidney blood flow by measuring the amount of urine produced per hour. However, in several classes of patients—to include those with acute renal failure and those who have received drugs, which artificially increase the production of urine—urine output measurements are not reliable indicators of kidney blood flow.

No device or technique exists rapidly and reliably to measure kidney blood flow at the level of the small blood vessels of the renal cortex in humans.

One noninvasive tool that has been tried is color Doppler ultrasound (CDUS), which displays mean velocity data and is useful in the study of large vessel blood flow. The slowest flow velocity detectable using color Doppler ultrasound is approximately 4 cm/sec. The ability to detect blood flow in smaller vessels did not exist until the advent of power Doppler ultrasound (PDUS), which provides spectral analysis of the received sound and integration of the resulting amplitude-frequency function to permit display of a perfusion index for each pixel as discussed by Rubin et al. in an article entitled "Power Doppler US: A Potentially Useful Alternative to Mean Frequency-based Color Doppler US," *Radiology*, 190:853–6 (1994) and Bude et al. in an article entitled "Power Versus Conventional Color Doppler Sonography: Comparison In The Depiction Of Normal Intrarenal Vasculature," *Radiology*, 192:777–80 (1994). PDUS is likely to be able to detect blood flow velocity of less than 1 cm/sec in ultrasound images.

In the PDUS mode, the ultrasound processor performs spectral analysis of the reflected sound, e.g., via fast Fourier transform. The amplitude (or power) of each received frequency is proportional to the number of red blood cells (RBCs) which are reflecting at that frequency. Frequency, in turn, is proportional to the velocity of the RBCs. Thus, a large number of RBCs moving at a low velocity should generate a high-power, low-frequency signal, whereas a smaller number of RBCs moving at high velocity should generate a low-power, high-frequency signal. The processor then integrates the power of the received signal over frequency to obtain a perfusion index for each pixel as discussed by Dymling et al. in an article entitled "Measurement of Blood Perfusion in Tissue Using Doppler Ultrasound," *Ultrasound in Medicine and Biology*, 1991:433–44 (1991).

In vitro phantom studies have shown that PDUS image intensity depends, as expected, on both the velocity and the concentration of reflecting particles. Commercially available ultrasound devices translate this numerical data into color output, in which the magnitude of the perfusion index is represented by color intensity. This color information is superimposed on the gray scale ultrasound image as illustrated by Parro et al. in an article entitled "Amplitude Information from Doppler Color Flow Mapping Systems: A Preliminary Study of the Power Mode," *J Am Coll Cardiol*, 18:997–1003 (1991).

Another advantage of PDUS is that it is not subject to aliasing (a signal wrap-around phenomenon seen in CDUS). The relative angle-independence of PDUS makes it less sensitive to inaccurate flow information based on an improper angle of insonation. One disadvantage of PDUS is a longer scanning time, which makes it more susceptible to motion and flash artifacts.

Clinical and animal studies employing PDUS have, as in a study conducted by the inventors and discussed later, demonstrated its utility in imaging the kidneys. Bude et al. demonstrated the increased sensitivity of PDUS over CDUS in depicting intrarenal and renal cortical flow in normal human kidneys, describing the latter as a non-pulsatile "blush." Durick et al. in an article entitled "Renal Perfusion: Pharmacologic Changes Depicted with Power Doppler US in an Animal Model," *Radiology*, 197:615–7 (1995), used an image analysis procedure to quantify changes in total renal perfusion as depicted by PDUS, following infusion of epinephrine and then papaverine into the renal artery of swine. Taylor et al., as discussed in an article entitled "Renal Cortical Ischemia in Rabbits Revealed by Contrast-Enhanced Power Doppler Sonography," *American Journal of Roentgenology*, 170:417–22 (1998), used contrast-enhanced PDUS to measure renal cortical perfusion during hemorrhagic hypotension in rabbits. The Taylor 5 et al. study found good correlation with blood flow as measured by radiolabelled microspheres; in contrast to the study conducted by the inventors, this correlation was not found when ultrasonographic contrast injection was not performed.

Akiyama et al. In their article entitled "Hemodynamic Study of Renal Transplant Chronic Rejection Using Power Doppler Sonography," *Transplant Proc,* 28:1458–60 (1996) proposed the use of power Doppler ultrasonography to represent blood flow; which however, offered no evidence that a power Doppler image would represent microvascular blood flow. They discussed the use of a power Doppler image focused on three areas of the kidney (the interlobar artery, the interlobular artery, and a portion of the outer cortex) to compare well functioning kidneys (S—Cr≦2.0 mg/dL) and poorly functioning kidneys (S—Cr>2.0 mg/dL) after a kidney transplant operation. The problem with this analysis, in part, is that going into the study it was known which kidneys were accepted and which kidneys were rejected by transplant patients. An explanation for the selection of these three locations is that Akiyama et al. assumed that these three areas would be more indicative of the status of the kidney than other areas of the kidney. These three sites as a result are not sufficiently indicative of the overall blood perfusion through the entire kidney. Another problem with their technique is that 32 gray-levels were utilized, thus offering less capability to accurately quantify perfusion in the PDUS image. Additionally, it is unclear from their article as to what a pixel index is and what method was used to calculate their mean number.

Furthermore, current methods of image analysis are labor-intensive and thus prone to mistakes and guess work at times.

Notwithstanding the usefulness of the above-described methods, a need still exists for a quantitative assessment of the ability of PDUS to measure changes in organ perfusion at the capillary level especially during ischemia, reperfusion, and more particularly following burn injury.

Ill. SUMMARY OF THE INVENTION

This invention provides a reliable indicator of the blood flow through the tissues of the cortex of the kidney by analyzing a PDUS image. More specifically, the intensity of the PDUS image correlates with renal cortex blood flow. This correlation exists during ischemia, reperfusion, and following burn injury.

An objective of the invention is to provide an accurate and reliable indication of the blood flow through an organ such as a kidney. A more particular objective is to predict the microvascular blood flow through the kidney.

A further objective of the invention is to have a noninvasive technique for measuring blood flow through an organ.

Another objective of the invention is to provide a quick numerical value indicating the state of microvascular blood flow through a particular organ to allow for a change in treatment of the patient, if necessary.

Another objective of the invention is to provide a numerical representation of blood flow through a kidney that may be used in conjunction with the diagnosis to determine whether there is sufficient renal cortical flow.

An advantage of the invention is the ability to determine a numerical representation of blood flow through any selected organ and particularly the kidney.

Another advantage of the invention is the determination of a numerical representation that correlates to blood flow through the entire organ by focusing on the smallest blood vessels.

Another advantage of the invention is an accuracy of a representation of blood flow that has not occurred in prior methods, in part, because of a lack of resolution.

A further advantage of the invention is the elimination of the anatomical features of the organ.

IV. BRIEF DESCRIPTION OF THE DRAWINGS

FIGS. 1(*a*) and 1(*b*) illustrate a flowchart and pictorial representations, respectively, of the preferred embodiment of the method.

FIG. 20(*b*) shows data points illustrating the relationship between renal artery flow and power Doppler ultrasound image intensity (PDUSII).

V. DETAILED DESCRIPTION OF THE DRAWINGS

Figure 1A:
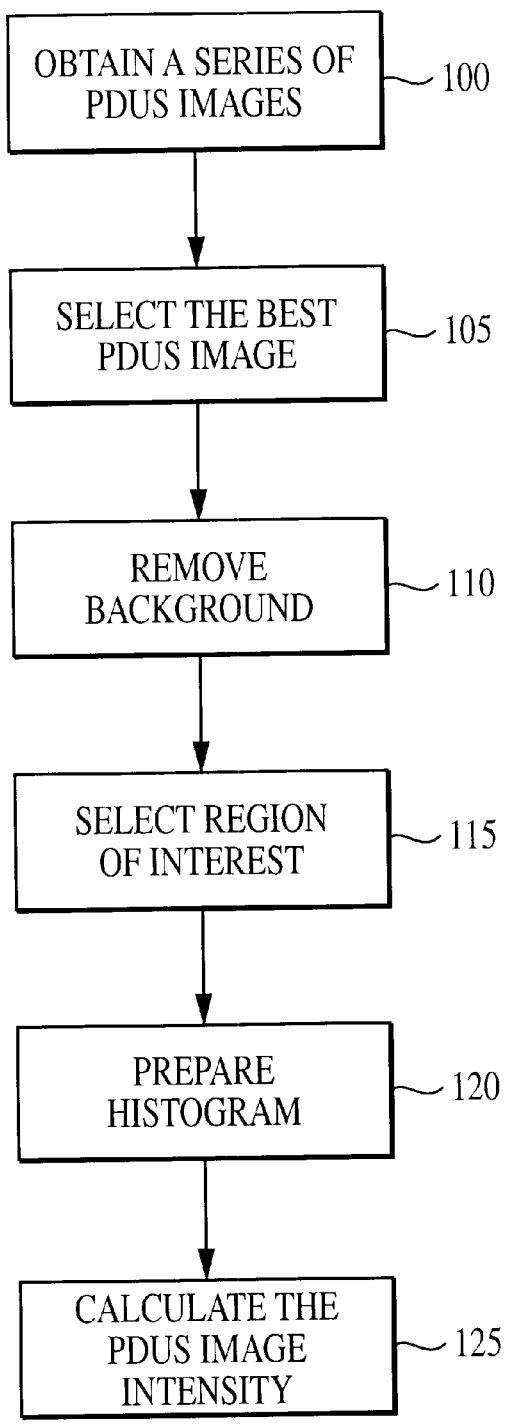
Figure 1B:
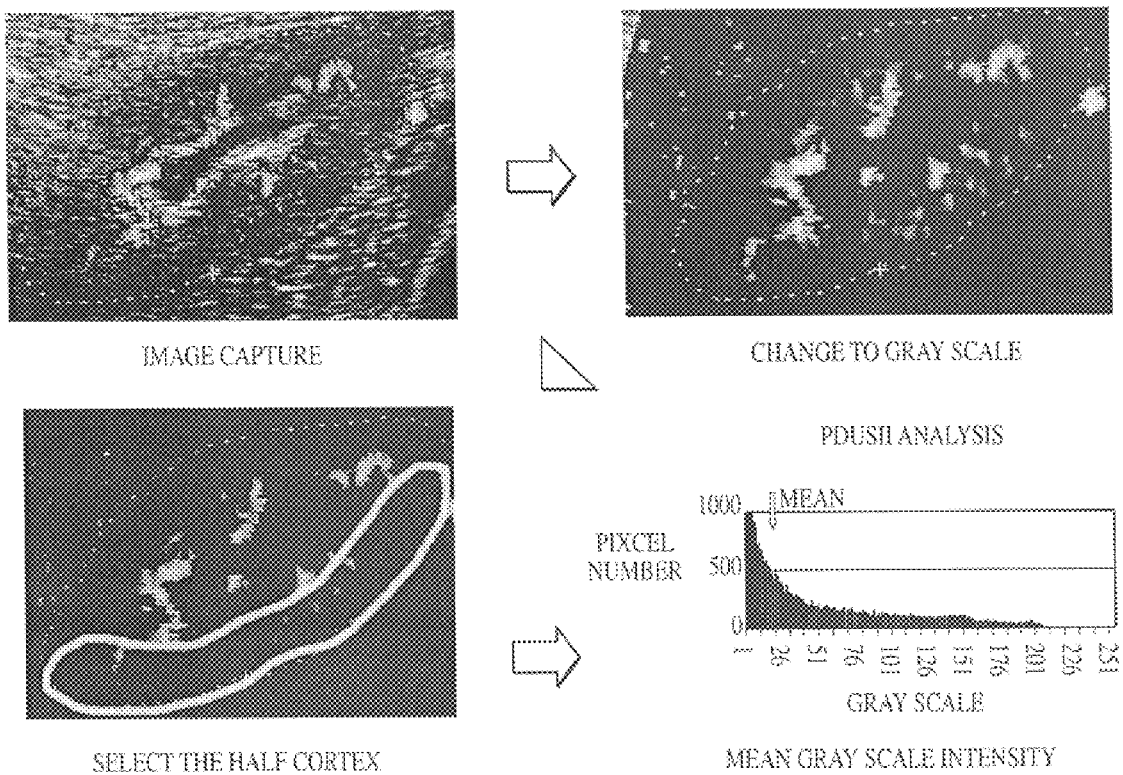

FIGS. 1(a)–(b) illustrate the method of the invention as a flowchart and a series of examples, respectively. Preferably the method includes six core steps with various alternative embodiments adding additional steps as well become apparent based on the described implementation. The first step 100 preferably is to take a series of power Doppler ultrasound (PDUS) images with an ultrasound device such as the Powervison SSA-380A (Toshiba America Medical Systems, Inc., Tustin, Calif.) and a transducer such as the 3.75 MHz convex transducer (Toshiba America Medical Systems, Inc., Tustin, Calif.). The next step 105 preferably is to select the PDUS image with the richest-appearing flow. The next step 110 preferably includes removing the background by dropping the lower gray-scale levels, for example, the gray-levels in the range of 0–30, preferably including the end points, by changing these levels to pure black. This step may be removed depending upon the index used to evaluate the numerical representation. Preferably, the next step 115 includes selecting a portion of the image that excludes larger vessels such as the hilum region of the kidney to form a region of interest. A histogram preferably is then performed on the region of interest such that the gray-levels are preferably expanded from a range of 31–255 to a range of 0–255 in step 120. Preferably, the next step 125 is to calculate the PDUS image intensity using the following equation:

$$PDUS \text{ image intensity} = \frac{\sum L_k P_k}{\sum P_k}$$

where $L_k$ is gray-scale level, $P_k$ is number of pixels as a function of gray-scale level, and $\Sigma P_k$ is the total number of pixels within the region of interest. The variable k is for the range of gray-levels present in the image. "PDUS image intensity" indicates the relative perfusion of the region of interest. The higher the PDUS image intensity is the more viable the organ is because the PDUS image intensity is a score that indicates the blood flow level through the organ, in particular, the flow through the smaller blood vessels. Additionally, the higher the PDUS image intensity is, the less need there will be for resuscitation fluids to be given to a burn patient.

Figure 2:
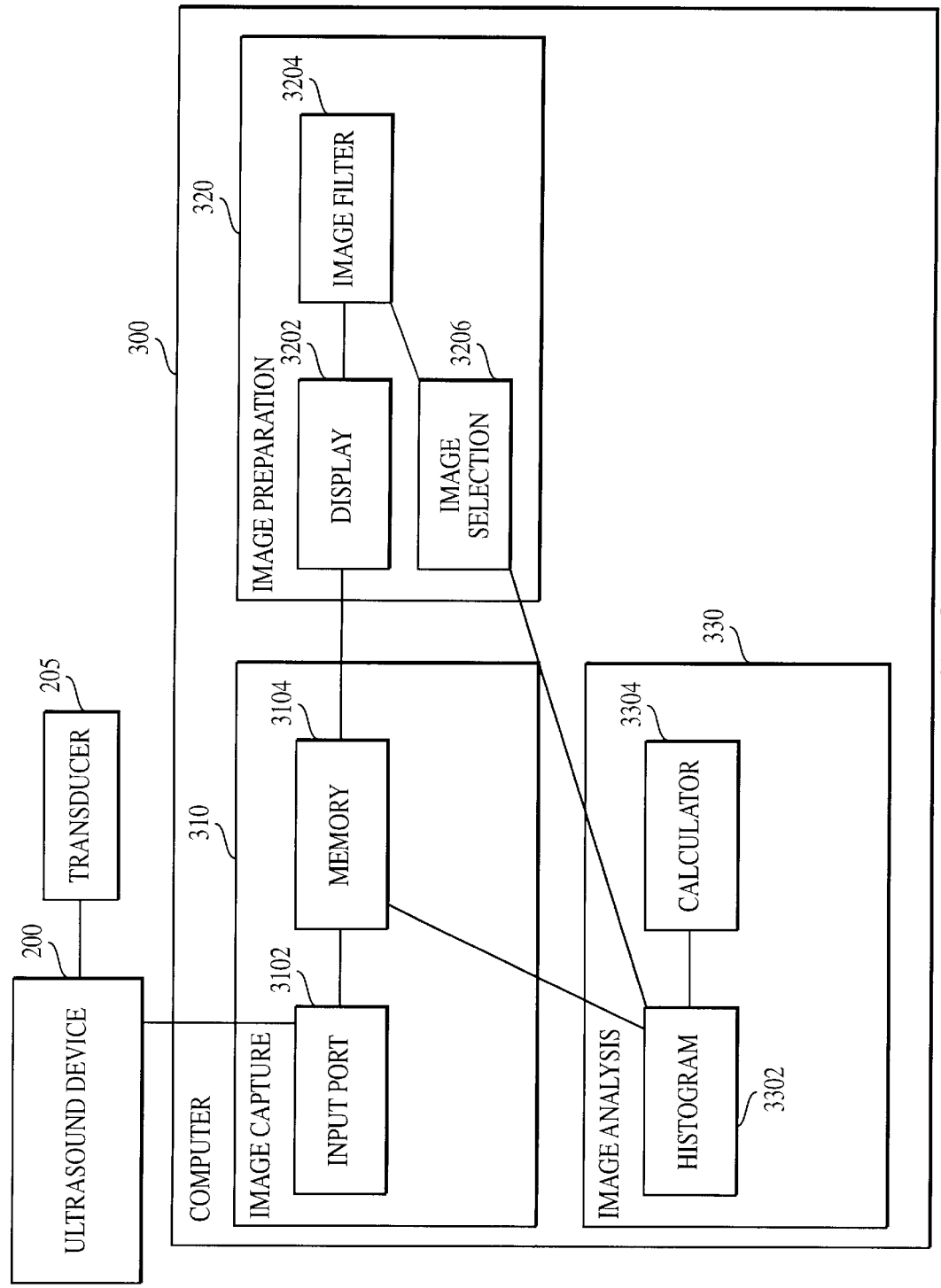
FIG. 2 depicts a block diagram of the preferred embodiment for an apparatus of the invention.

FIG. 2 illustrates a preferred embodiment for a system to perform the method. The system preferably includes an ultrasound device 200, a transducer 205, and a computer with processing software 300 (means for processing). The computer and software 300 preferably is able to capture images from the ultrasound, prepare the image, and analyze the image. Preferably, the image capture portion 310 (or means for capturing an image) includes a port 3102 for receiving the image from the ultrasound device 200 and memory 3104 for storing the image in a computer readable form. The memory 3104 preferably is at least one of the following: random access memory (RAM); in read only memory (ROM); on a storage device like a hard drive, disk, compact disc, punch card, tape or other computer readable material; in virtual memory on a network, a computer, an intranet, the Internet, the Abilene Project, or otherwise; on an optical storage device; on a magnetic storage device; and/or on an EPROM. The image preparation portion 320 (or means for preparing an image) preferably includes a display 3202 for displaying the series of images taken to allow the user to select the desired image, a component 3204 such as software for removing the lower gray-levels from the image, and a component 3206 such as software for selecting the region of interest. The image analysis portion 330 (or means for analyzing an image) preferably includes a component 3302 such as software for preparing a histogram of the region of interest and a component 3304 such as software calculating the PDUS image intensity. One of ordinary skill in the art will realize based on this disclosure that the image analysis portion 330 may include the component 3206 for selecting of the region of interest instead of the image preparation portion 320.

Alternatively, the image preparation portion 320 may include software to determine the image having the richest-appearing flow of blood by contrasting the images with each other to determine the image having the most blood flow activity present using digital subtraction. The image having the highest average positive difference over the other images will be the image with the richest-appearing flow of blood. This procedure may be performed, for example, by Toshiba's contrast imaging package.

A further modification is to have the image preparation portion 320, or the image analysis portion 330 depending the exact implementation, determine the region of interest based on the area of the image opposite that of the region having a large presence of blood flow through large vessels such as the vein and artery passing through the hilum region of the organ. The resulting region of interest then will be the portion of the cortex opposite that of the hilum. The determination preferably will be made by an internal contrasting of different regions of the organ present in the image, thus the region having the largest blood flow will be excised and not included in the region of interest. Preferably, the region of interest will not include the periphery of the organ to ensure that only the organ is being analyzed.

A further alternative embodiment is for the processing means 300 to be at least one of the following: electronic hardware as either dedicated equipment or equipment internal to a computer, software embodied in computer readable material for use by computers, software resident in memory or a programmed chip for use in computers or dedicated equipment such as a application specific integrated circuit (ASIC), or some combination of both hardware and software. The dedicated equipment may be part of a larger device that would complement the dedicated equipment's purpose.

One implementation of the preferred embodiment of the method and the apparatus is as follows.

A power Doppler sonography was performed by a single examiner using a Powervison system 200 such as the Powervison SSA-380A (Toshiba America Medical Systems, Inc., Tustin, Calif.) and a 3.75 MHz convex transducer 205 (Toshiba America Medical Systems, Inc., Tustin, Calif.). The Powervision system 200 was set to remove the anatomical features from the image. A series of images were obtained and stored continuously over one minute. The Powervision allows for the inclusion of reference markings such as the dashed kidney shaped marking present, for example, in three of the boxes illustrated in FIG. 1(b). The kidney shaped object was added to each image to assist in identifying where the kidney is in the PDUS image.

All of the stored images were reviewed and the image with the richest-appearing flow was selected. The gray-scale version of the PDUS image, which incorporates PDUS image intensity data but omits gray-scale anatomic details, was saved to a computer, such as a Dell® laptop, as a JPEG file using a Snappy frame grabber (Play Inc., Cordova, Calif.). Image preparation and analysis were performed using Adobe Photoshop® version 4.01 software (Adobe Systems Inc., San Jose, Calif.) for image manipulation and Optimas version 5.22 software (Media Cybernetics, Bothell, Wash.) for image analysis.

Figure 3:
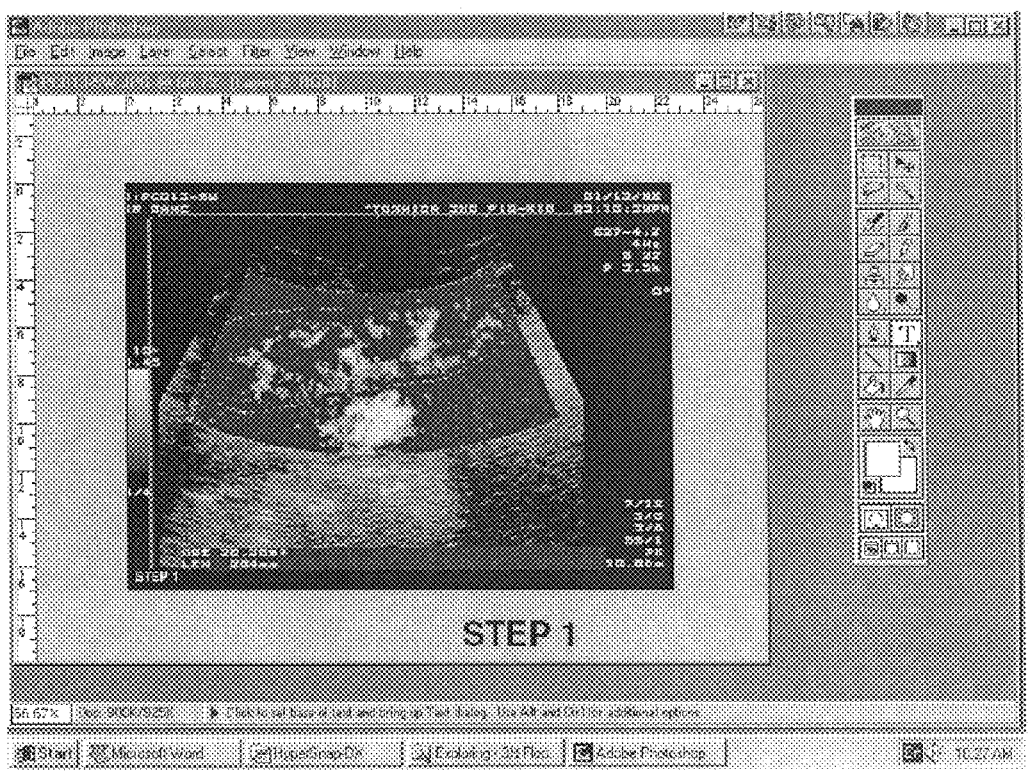
FIG. 3 illustrates the opening of a JPEG file into Adobe Photoshop® in an implementation of the invention.
Figure 4:
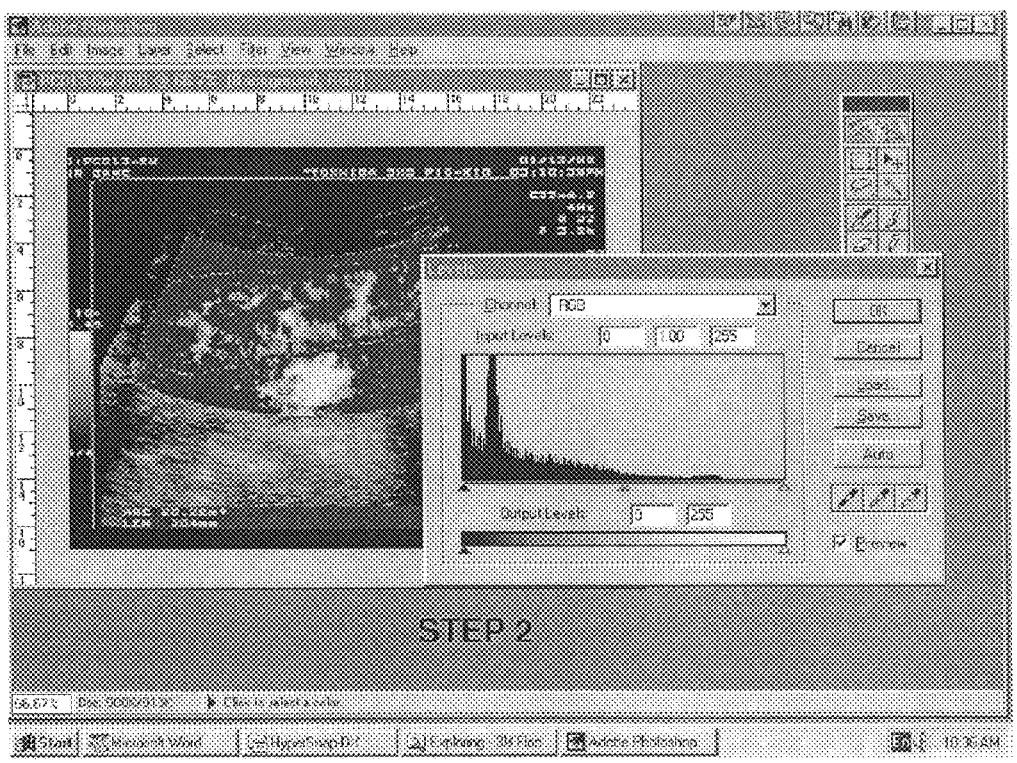
FIG. 4 depicts the selecting of the Levels function in Adobe Photoshop® in the implementation of the invention.
Figure 5:
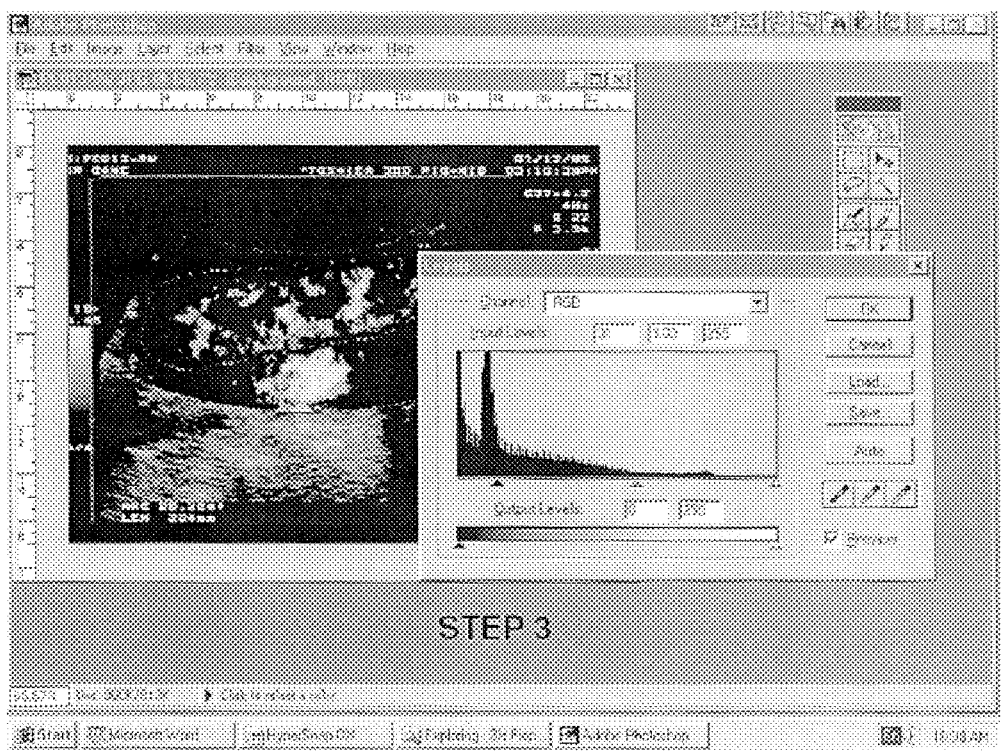
FIG. 5 illustrates the adjustment of the gray-levels of the image in Adobe Photoshop® in the implementation of the invention.
Figure 6:
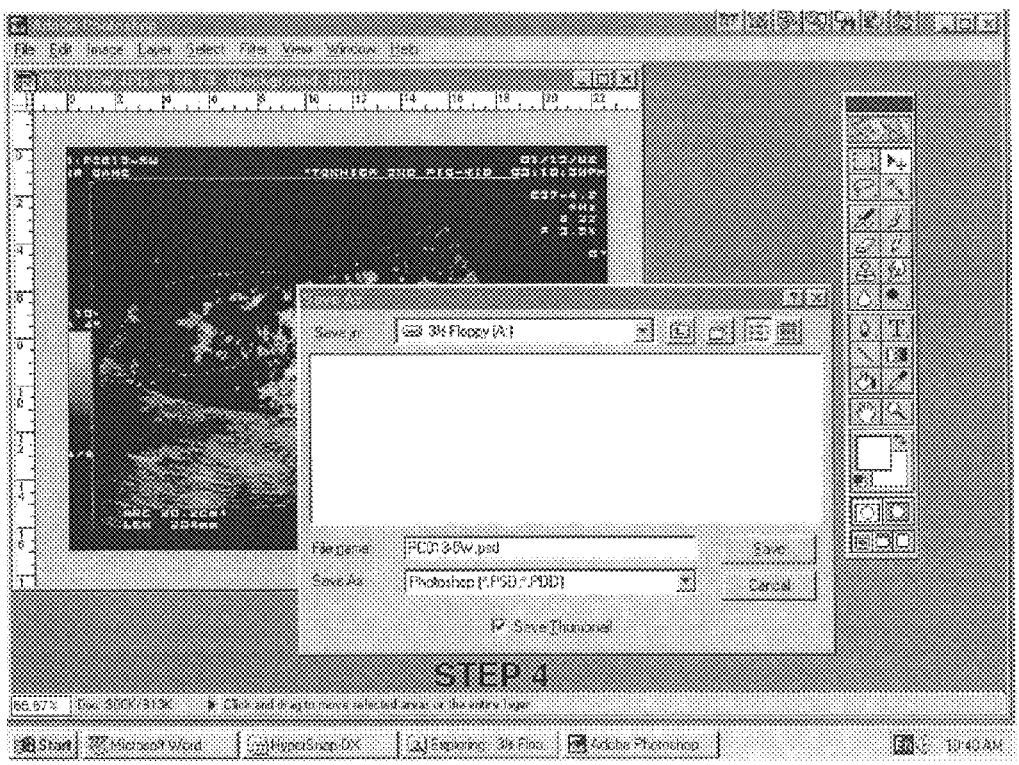
FIG. 6 depicts saving the image as a Photoshop® format file in Adobe Photoshop® in the implementation of the invention.

The image preparation and analysis steps discussed below are illustrated in FIGS. 3–15. The first step is to open the JPEG file in Photoshope® as illustrated in FIG. 3. The next step shown in FIG. 4 is to delete the image background using the Adjust Levels function. On the pull-down Photoshop® menu, Image was selected, followed by Adjust, followed by Levels. The next step is illustrated in FIG. 5 as being the adjustment of the gray-levels, which in the case of the Toshiba ultrasound system means changing the gray-levels in the range of 0–30 so that the background is black, gray-level 0. Although with different ultrasound systems from other manufacturers, the background gray-levels may vary to some degree; however, approximately the first grouping of gray-levels that form a spike as illustrated in FIGS. 4 and 5. The first spike will typically include the gray-levels in the lowest 25% to 35% of the available gray-levels, which represent the dark grays. The purpose of this step is to remove all of the dark gray-levels from the image by turning those particular pixels into black. The step illustrated in FIG. 6 is to save the file as a Photoshop (.psd) file; however, any graphic format that is capable of being processed by the utilized software.

Figure 7:
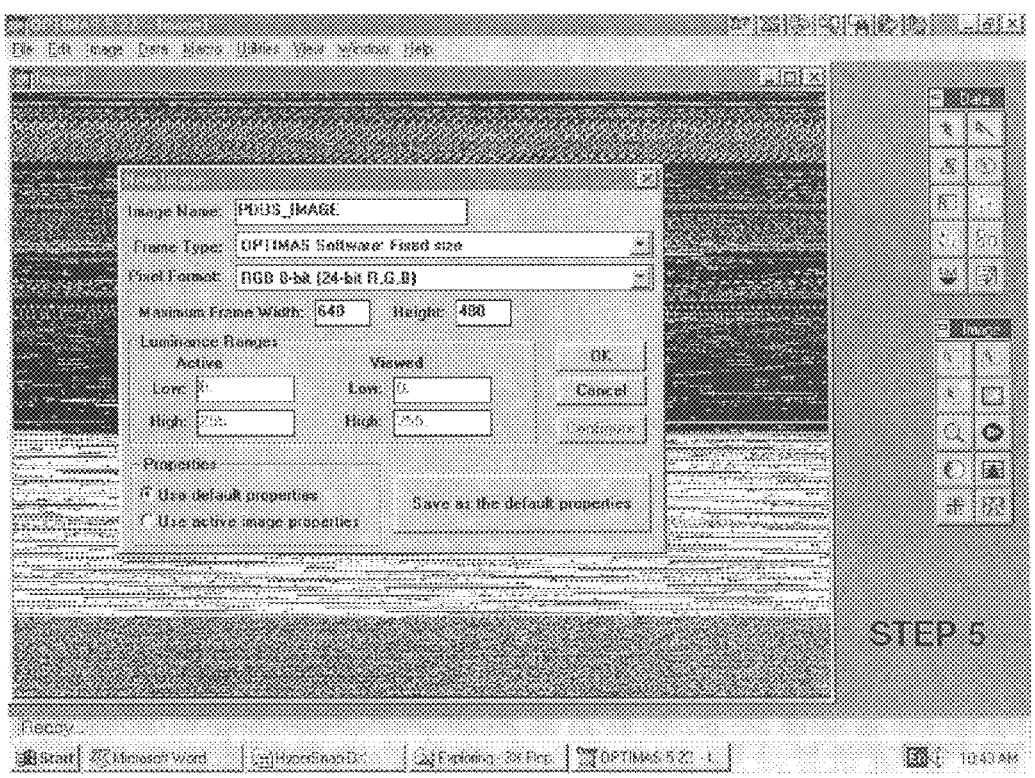
FIG. 7 illustrates the selection of the file saved in FIG. 6 in the implementation of the invention.
Figure 8:
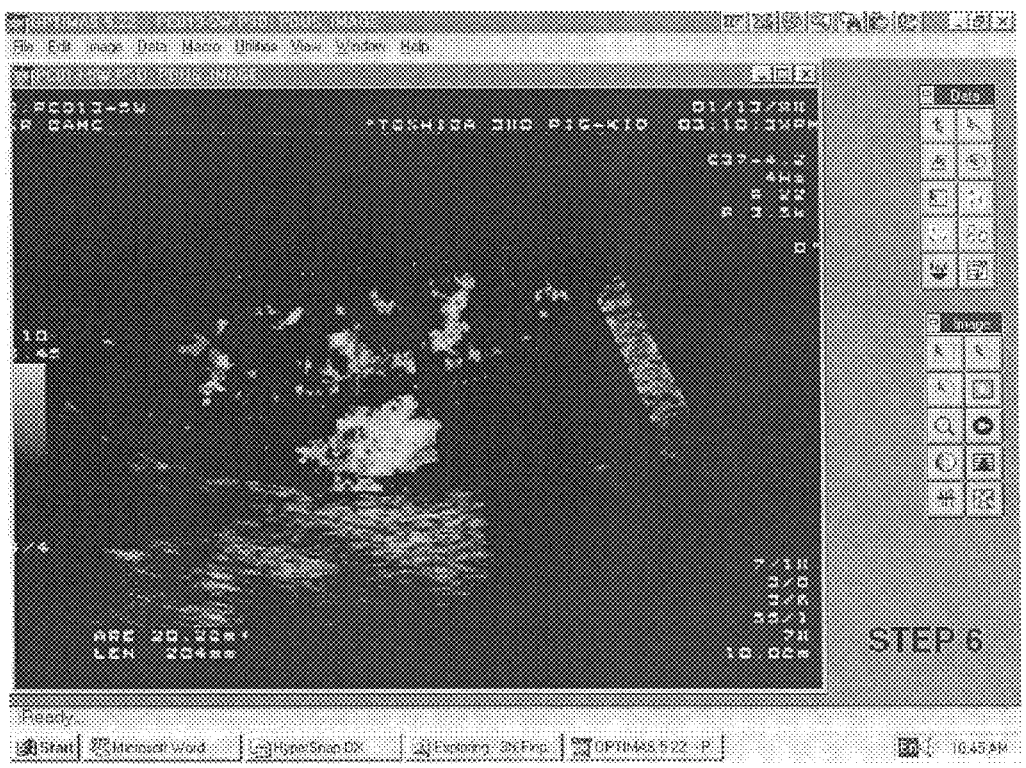
FIG. 8 depicts the opened file saved in FIG. 6 in Optimas in the implementation of the invention.

The next step is illustrated in FIGS. 7 and 8, which is to open the saved image in Optimas.

Figure 9:
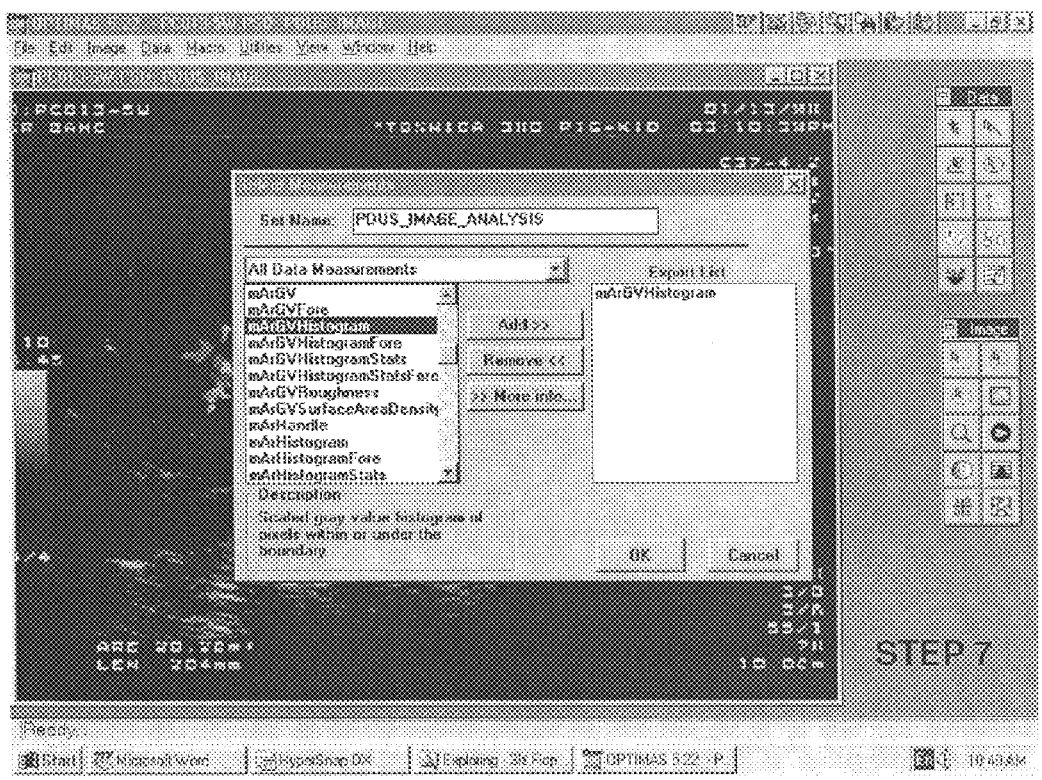
FIG. 9 illustrates the selection of a measurement in Optimas in the implementation of the invention.
Figure 10:
FIG. 10 depicts the selection of the file format for the file to store the measurements selected in FIG. 9 in Optimas in the implementation of the invention.
Figure 11:
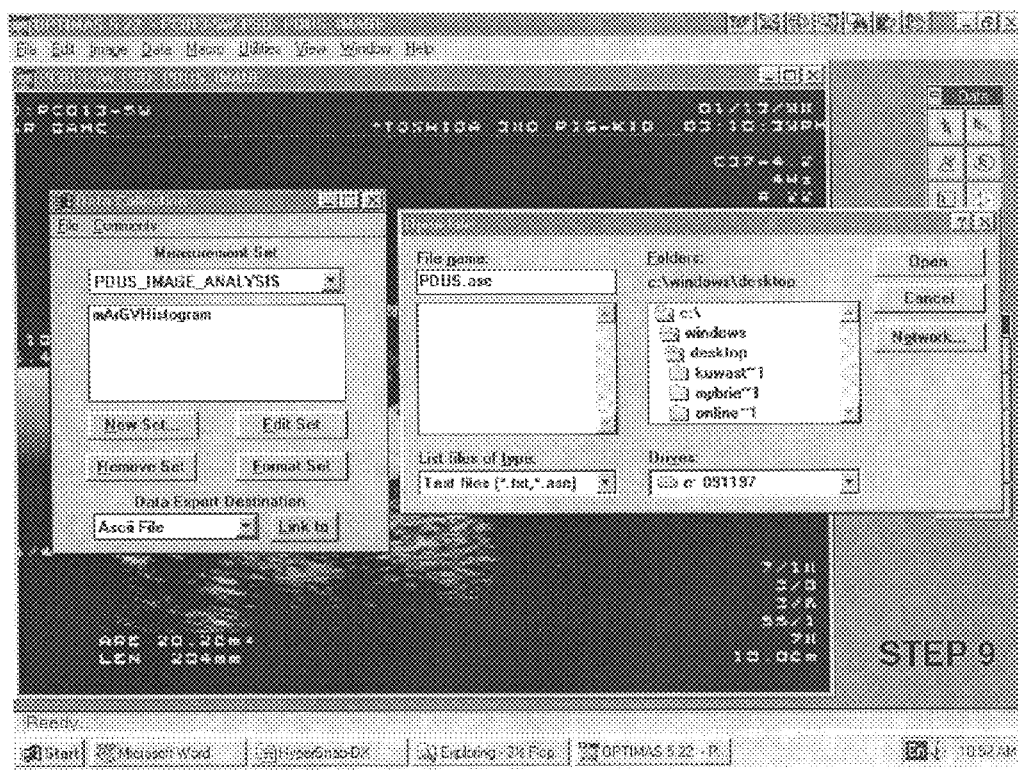
FIG. 11 illustrates the naming of the measurement file referenced in FIG. 10 in Optimas in the implementation of the invention.
Figure 12:
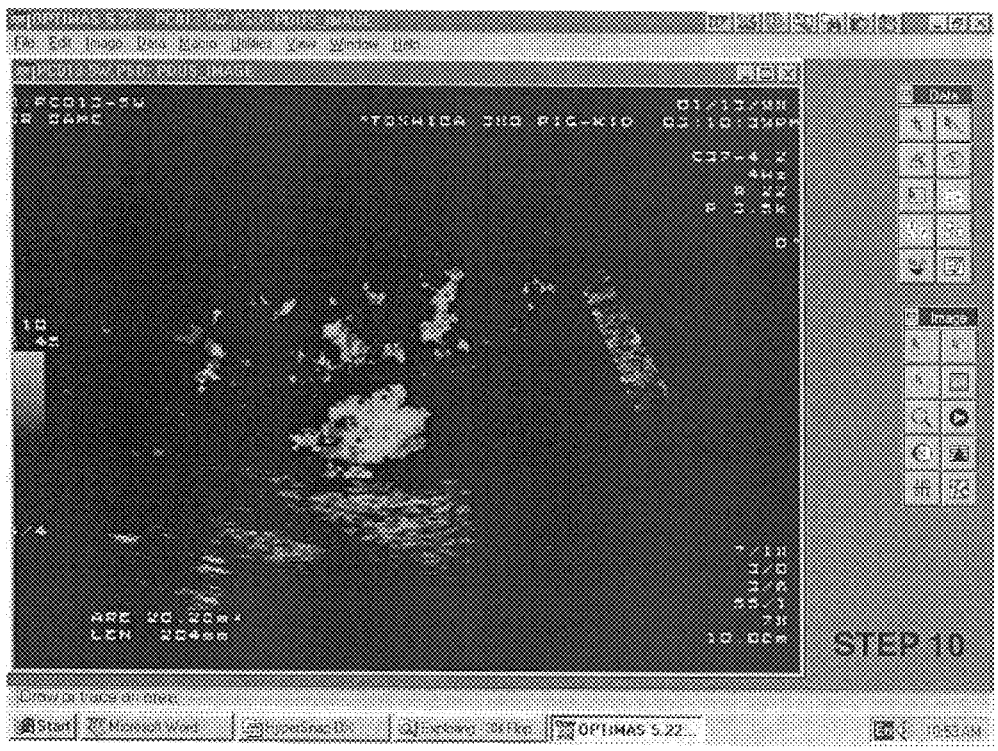
FIG. 12 depicts the selection of a freehand drawing element to select a region of interest in Optimas in the implementation of the invention.
Figure 13:
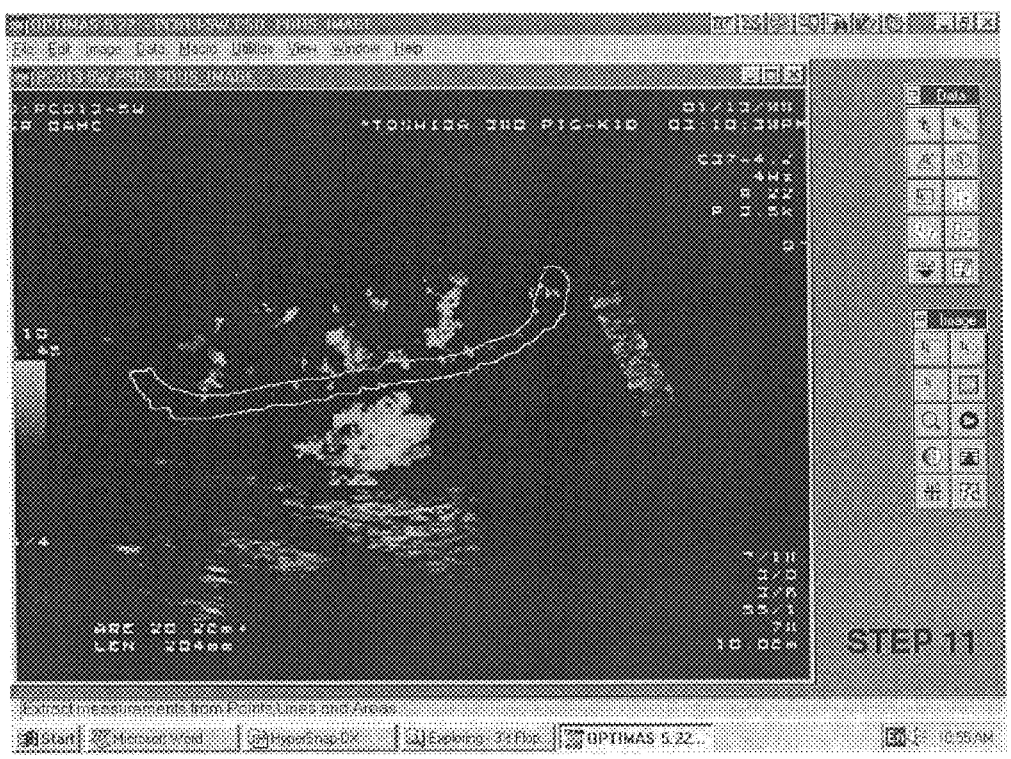
FIG. 13 illustrates the selection of the measurement extraction button in Optimas in the implementation of the invention.
Figure 14:
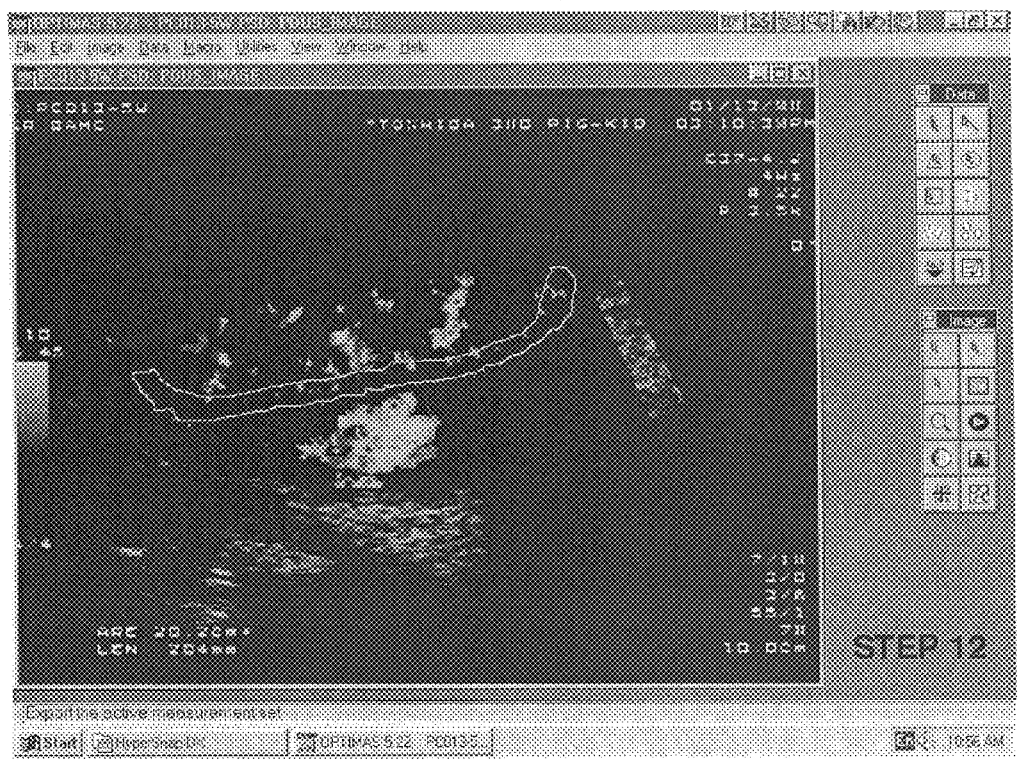
FIG. 14 depicts the selection of active measurement set exportation button button in Optimas in the implementation of the invention.

The next three steps shown in FIGS. 9–11 may be placed after the selection of a region of interest step illustrated in FIG. 12. The step illustrated in FIG. 9 is the selection of mArGvHistogram function from the Select Measurements menu within in Optimas. The selection of this function provides for the remaining gray-levels to be expanded out to the full range of possible gray-levels and allows for the counting of the number of pixels at each gray-level. In this implementation this means expanding gray-levels 31–255 out to gray-levels 0–255. The following two steps include selecting the type of output file format as ASCII and a file name as illustrated in FIGS. 10–11, but the file format may also be in Microsoft® Excel format if Optimas 6.5 or similar software package that allows for this file format is utilized instead of Optimas 5.2. FIG. 12 illustrates the step of using a freehand drawing tool, available for example by using the Data toolbar, to mark a region of interest. The region of interest preferably is the portion of the cortex opposite the hilum so as not to include the big vessels in the image, because the analysis is best performed with the smaller vessels. The smaller vessels on the cortex will provide an accurate representation of the blood flow throughout the chosen organ, which in this example is the kidney. The region of interest preferably is about one-half of the renal cortex. FIGS. 13 and 14 illustrate the solid outlined region of interest, which in this example is a crescent shape, produced by step illustrated in FIG. 12.

The next step is illustrated in FIG. 13, which illustrates the measurement extraction button being selected to start the mArGvHistogram function. The mArGVHistogram function was used to create a scaled gray value histogram of pixels within the region of interest. The next step is illustrated in FIG. 14 and shows the active measurement set exportation button being selected to send the data produced by the mArGvHistogram function into a file.

Figure 15:
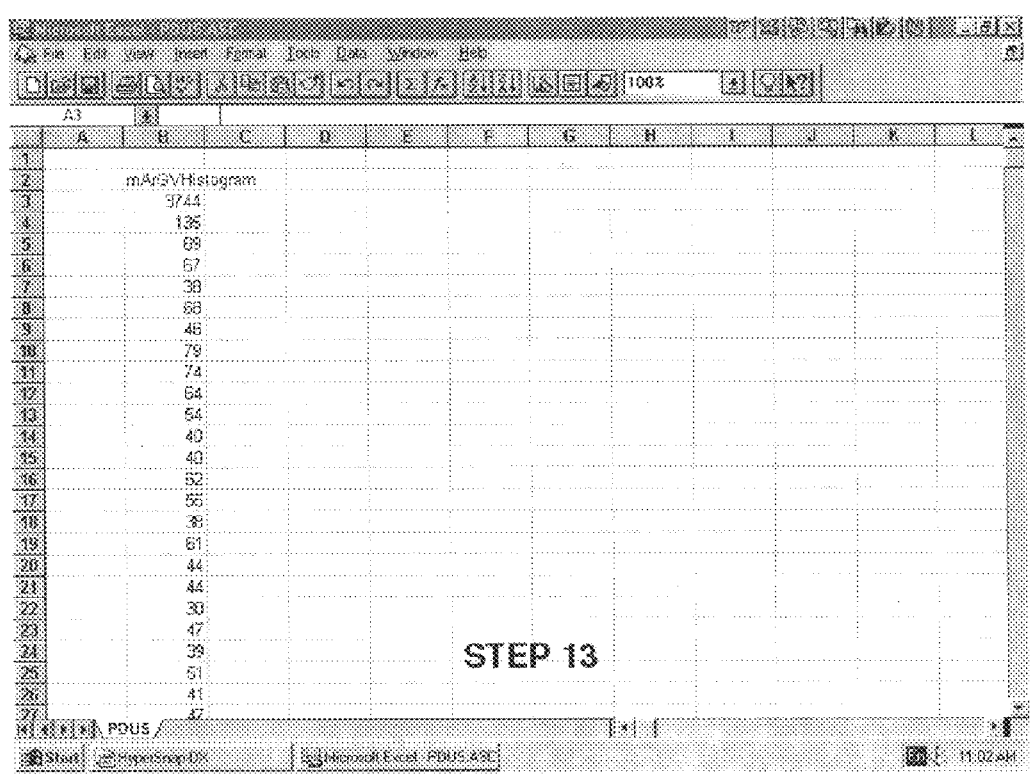
FIG. 15 illustrates the data stored in the data file as produced by the selected measurement in Microsoft® Excel.
Figure 16:
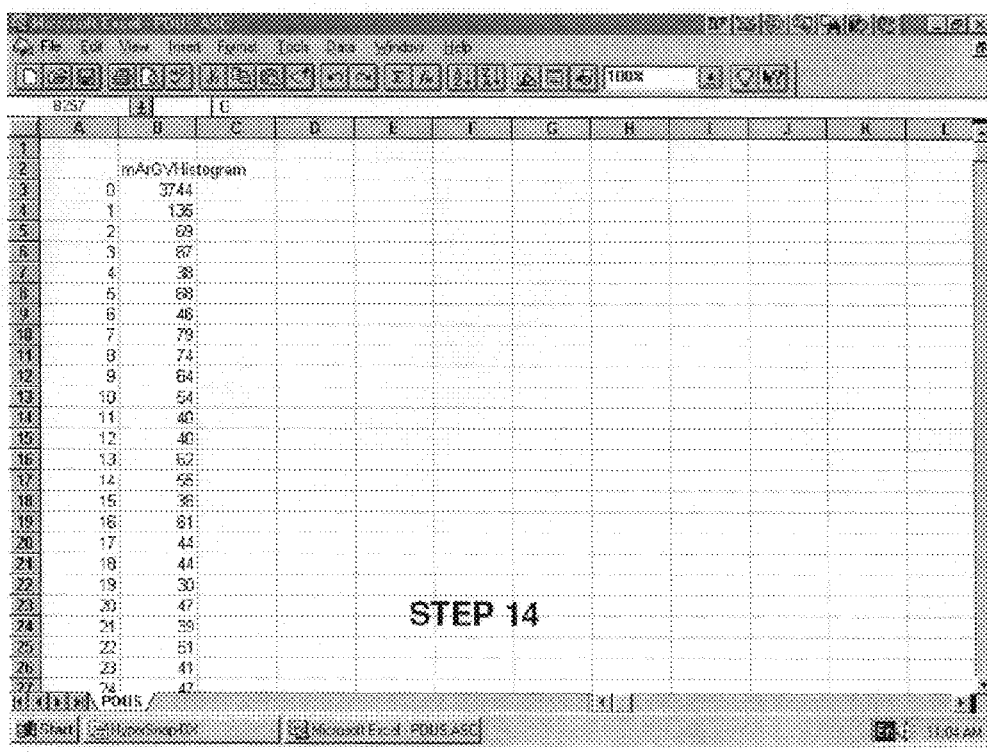
FIG. 16 depicts the addition of gray-levels in column A of FIG. 15.
Figure 17:
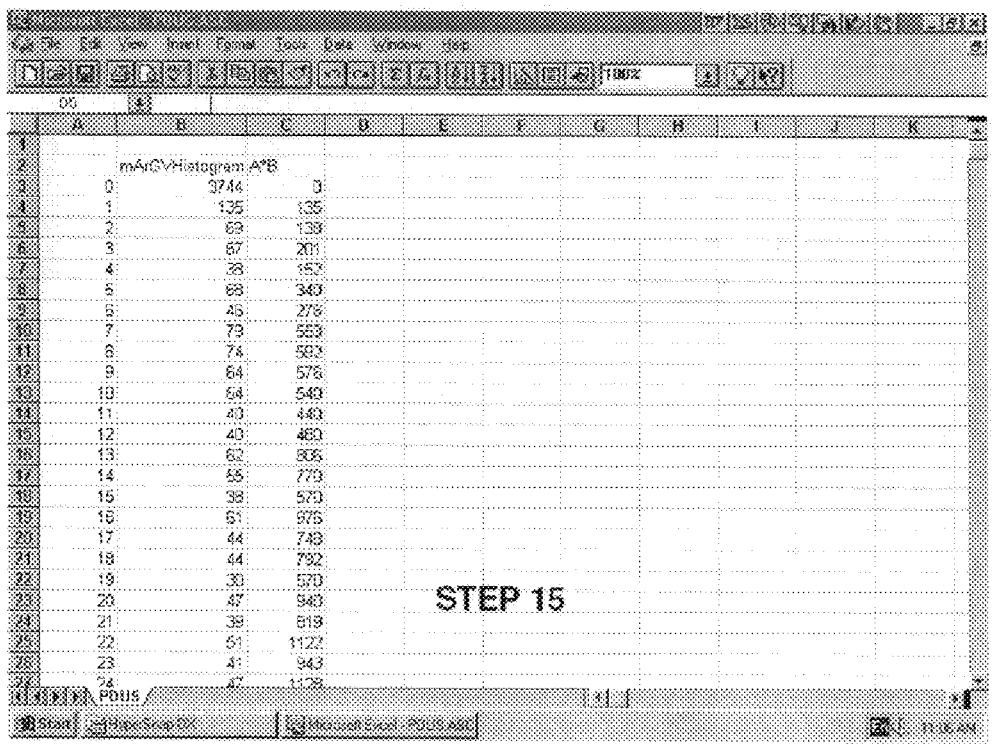
FIG. 17 illustrates the inclusion of a multiplication function in column C of FIG. 16.
Figure 18:
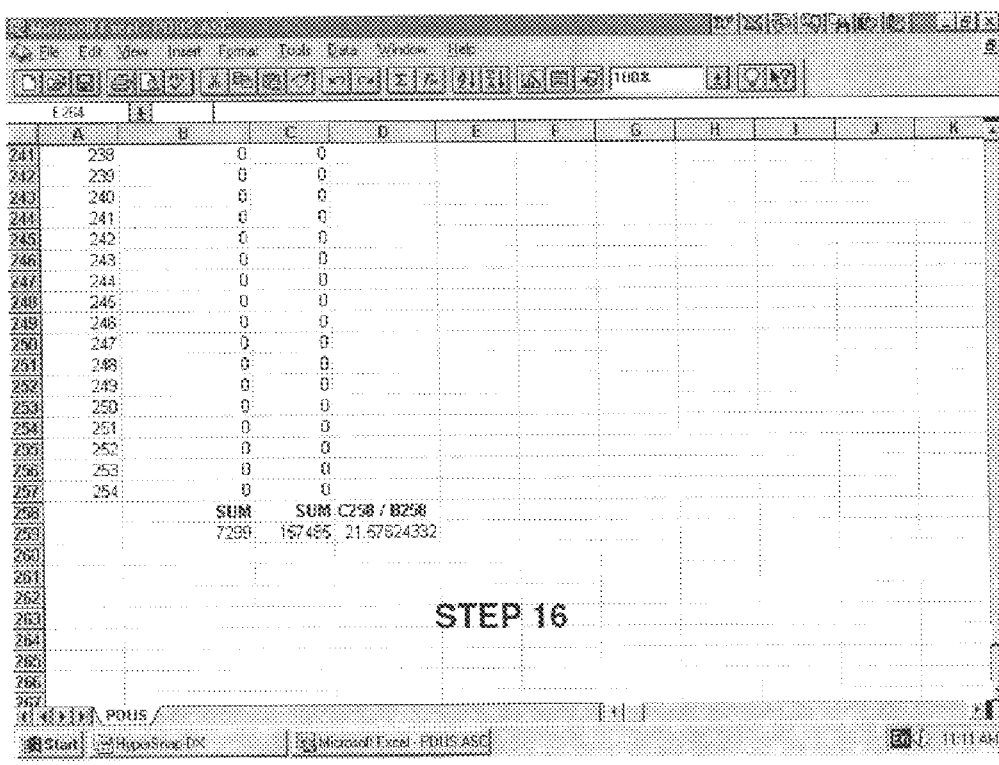
FIG. 18 depicts the sums and PDUS image intensity for this particular set of data.

The next step is to open the data file in a spreadsheet program such as Microsoft® Excel as illustrated in FIG. 15. Column B contains the histogram for the region of interest. The next step is illustrated in FIG. 16 and includes the adding of the gray-levels into column A. FIG. 17 illustrates the next step of multiplying column A with column B and inserting the result into column C for each gray-level (a scale of 0–255, with 0=black and 255=white). The PDUS image intensity is the sum of these products (sum of column C) was divided by the total number of pixels within the region of interest (sum of column B) as illustrated in FIG. 18. This calculation is depicted in FIG. 18 as the summing of columns B and C and the resulting calculation of the following equation, which produces the PDUS image intensity value for the region of interest:

$$PDUS \text{ image intensity} = \frac{\sum L_k P_k}{\sum P_k}$$

were $L_k$ is gray-scale level, $P_k$ is number of pixels as a function of gray-scale level, and $\Sigma P_k$ is the total number of pixels within the region of interest. The variable k is for the range of gray-levels present in the image.

One alternative to the above-described implementation is to use Optimas 6.5 to receive the image directly from the power Doppler ultrasound machine instead of using the intermediary components of Adobe Photoshop® and the Snappy frame grabber to perform the image processing as discussed above.

"PDUS image intensity" was hypothesized to indicate the relative perfusion of the region of interest, and in the experimental validation of this technique was correlated with microvascular blood flow as determined by fluorescent microspheres.

The preferred method and the correlation between renal artery flow and PDUS image intensity has been verified by a study conducted in part by the inventors. The study verifies the validity of the above-discussed implementation to analysis images taken from a porcine model of renal arterial occlusion and reperfusion, and then in a porcine model of burn shock. The porcine model was chosen in part because the functional characteristics of their cardiovascular systems closely resemble those of man, and because swine and man are unique in possessing multipapillate and multi-pyramidal kidneys. The kidneys of both species have predominantly shortlooped nephrons (swine 97%, human 86%). Additionally, the blood flow per 100 g of kidney tissue is similar in both humans and swine.

The ischemia/reperfusion study involved five male Yorkshire swine (mean weight 18.4 kg, range 16.4–19.4 kg), which were fasted overnight. On the morning of the study they were sedated with intramuscular tiletamine/zolazepam (3 mg/kg, Ft. Dodge Laboratories, N. W. Fort Dodge, Iowa) and atropine (0.1 mg/kg, Vedco, Inc., St. Joseph, Mo.). 10 minutes later general anesthesia was induced using isoflurane (Ohmeda Caribe Inc., Gayama, PR) administered through a nose cone. The pigs were then intubated with a 6.0–8.0 mm endotracheal tube (The Kendall Co., Mansfield, Mass.). The right carotid artery was cannulated with a 1.9 mm catheter (Becton Dickinson and Co., Sparks Md.) and the jugular vein was cannulated with 7 F introducer (Arrow International Inc. Reading, Pa.). A 1.9 mm right femoral arterial line (Becton Dickinson and Co., Sparks, Md.) was placed and advanced into the descending aorta to the level of xiphoid process to remove blood for fluorescent microsphere determination. A left anterior thoracotomy was performed. A 1.9 mm catheter (Becton Dickinson and Co., Sparks, Md.) was placed into the left atrium for the injection of fluorescent microspheres, and secured with a purse-string suture. A chest tube (12F, Argyle-Sherwood Medical St., Louis, Mo.) was placed and connected to underwater seal and the thoracotomy was closed. By a right retroperitoneal approach the right renal artery was exposed and a vascular occluder (OC3, In Vivo Metric Systems, Healdsburg, Calif.) and an ultrasonic flow probe (3RB, Transonic Systems Inc., Ithaca, N.Y.) were placed transversely. After filling the retroperitoneal space with ultrasound transmission gel (Graham-Field Inc., Hauppauge, N.Y.) the wound was closed in layers.

The animals were immobilized in the left lateral decubitus position on a warming blanket, and were mechanically ventilated with isoflurane (1–2%). Tidal volume was maintained at 13 cc/kg, and the rate was adjusted to maintain $PCO_2$ at approximately 40 mmHg. The animals received Lactated Ringer's solution (50–100 ml/hr) and Fentanyl citrate (0.02–0.03 mg/kg/hr) continuously and pancuronium bromide (Gensia Laboratories, Ltd, Irvine, Calif.) in 2 mg doses every 30 minutes. Arterial blood pressure was monitored and systolic pressure was maintained over 90 mmHg.

The vascular occlusion and imaging began when the arterial blood pressure stabilized at a systolic pressure over 90 mmHg, the ultrasonic flow probe was activated. Grayscale ultrasonography of the right kidney was performed, a PDUS image was obtained, and fluorescent microspheres were injected as described below. Then the vascular occluder was inflated until the renal artery blood flow as determined by the ultrasonic flow probe was reduced to 75% of baseline. Another PDUS reading was taken and injection of fluorescent microsphere was again performed. This procedure was repeated with flow at 50%, 25%, and then following release. Several minutes elapsed after each change in cuff pressure, to ensure stable vital signs and arterial flow. Animals were euthanatized with sodium pentobarbiatal (25 mg/kg, Sigma Chemical Co., St Louis Mo.) and an overdose of a 20% potassium chloride (15–20 ml, International Medication Systems, Ltd., El Monte, Calif.) after the final measurement.

The burn study was broken into three parts: 1) burn depth, 2) burn size, and 3) renal blood flow.

The burn depth portion of the burn study involved two male and one female Yorkshire swine (mean weight 12.0 kg, range 9.5–14.0kg) that were given a scald injury to determine the exposure time required to produce a full-thickness burn. General anesthesia was induced and animals were intubated as described above. The right jugular vein was cannulated with a 7 F introducer (Arrow International Inc., Reading, Pa.). Following premedication with 0.5 mg fentanyl citrate (Elkins-Sinn, Inc., Cherry Hill, N.J.), deep general anesthesia was induced by hyperventilation with 5% isoflurane for 5 minutes. A dorsal injury representing approximately 10% of the total body surface area (TBSA) was inflicted by immersion in 207 F. degree water for 15 seconds. Animals were allowed to recover in metabolic cages, and then extubated. Thereafter, they were given food and water ad libitum, and received intravenous 0.15 mg buprenorphine hydrochloride (Reckitt & Colman Products, Richmond, Va.) as needed, for pain. A 1% silver sulfadiazine cream (Knoll Pharmaceutical Co., Mount Olive, N.J.) was applied every 12 hours to the burn and animals were given Lactated Ringer's solution (50–200 ml/hr) continuously. After 24 hours postburn, the animals were euthanatized with sodium pentobarbital (25 mg/kg) and an overdose of a 20% potassium chloride (15–20 ml). After death the depth of the injury was determined by histological examination of full-thickness biopsies taken from the center and margins of dorsal burns. Depth of the injury was determined by standard histopathological criteria by a veterinary pathologist.

The burn size portion of the burn study involved fifteen male Yorkshire swine (mean weight 20.3 kg, range 15.5–26.7 kg) that were used to determine the "lethal area 50 percent" (LA50) for scald injury in the absence of resuscitation, and thus to determine a burn size sufficient to produce shock during the first 24 hours postburn. General anesthesia was induced and animals were intubated described as above. The right carotid artery was cannulated with a 1.9mm catheter and the jugular vein was cannulated with a 7 F introducer for infusion. A tracheotomy was performed to facilitate mechanical ventilation throughout the experiment. Following premedication with 0.5 mg fentanyl citrate and hyperventilation with 5% isoflurane for 5 minutes, scald injury was performed by immersion under deep general anesthesia as described above, and various anatomic landmarks were used to ensure reproducibility of burn sizes within burn size groups. After scald injury animals were nursed and continuously monitored in an animal intensive care unit. They were received fentanyl citrate, (0.02–0.03 mg/kg/hr), pancuronium bromide (1.6–2 mg/kg/hr) and midazolam HCL 0.05–0.1 mg/kg/hr (Roche Pharma, Inc., Monati, PR) throughout the experiment. They were mechanically ventilated (Servo 900C, Siemens, Munich, Germany) in the volume control mode. Animals only received these drugs and received no fluid. 1% Silver sulfadiazine cream was applied twice a day to the burns. Heart rate and blood pressure were monitored continuously. 24 hours postburn, animals were euthanatized with sodium pentobarbital (25 mg/kg) and an overdose of a 20% potassium chloride (15–20 ml). The surface area burned in meters squared was estimated with the use of a cloth, onto which an outline of the burned area was traced. Body surface area was estimated by Meeh's formula: $A=0.097W^{0.633}$, where A is surface area in meters squared and W is body weight in kilograms. Total burn surface area burned as a percentage of body surface area was then calculated.

The renal blood flow portion involved eight male Yorkshire swine (mean weight 25.8 kg, range 23.2–28.7 kg) were used. The same procedures were followed as described above for the ischemia-reperfusion study, with the exception that the renal artery exposure was not performed. Postoperatively, the animals were transported to an animal intensive care unit where they were nursed on custom foam pads and continuously monitored. The position of the animals was changed every 2 hours. Animals were mechanically ventilated (Servo 900C, Siemens, Munich, Germany) throughout the experiment. Tidal volume was maintained at 13 cc/kg, and rate was adjusted to maintain $PCO_2$ at approximately 40 mmHg. They received continuous fentanyl citrate, (0.02–0.03 mg/kg/hr), pancuronium bromide (1.6–2 mg/kg/hr) and midazolam HCL (0.05–0.1 mg/kg/hr) throughout the experiment.

Each of the animals was then resuscitated after the arterial blood pressure stabilized with a systolic pressure over 90 mmHg, baseline studies were done. A 75% full thickness scald injury was then performed as described above, with immersion for 17 seconds at 207 F. Delayed resuscitation was initiated at postburn hour 6 according to the Parkland formula (4 ml Lactated Ringer's solution/total burn surface area/kg body weight/24 h), with infusion of the volume predicted for the first 8 h over postburn hours 6–8. At postburn hour 8 volume loading was performed to achieve a pulmonary capillary wedge pressure (PCWP) of 16 mmHg. Starting at postburn hour 10, dobutamine at 10 mcg/kg/min (Eli Lilly and Co., Indianapolis, Ind.) was infused, further to augment cardiac output. The purpose of these interventions was to permit evaluation of the accuracy of PDUS over a wide range of renal cortical blood flow levels.

There was a series of measurements taken before injury and every 2 hours thereafter, PDUS of the kidney and assessment of renal artery resistance index (RARTRI) measured by color Doppler ultrasound (CDUS) were performed. At the same time, injection of fluorescent microspheres was performed as described below. Pulmonary artery pressure, PCWP, central venous pressure, heart rate, systemic arterial pressure (Pressure Monitor 78354C, Hewlett-Packard, Waltham, Mass.) and urine output were measured every hour. Every 2 hours, cardiac output was measured by the themodilution technique (Oximeter/Cardiac output computer, SAT-2 Baxter Edwards Critical-Care, Irvine, Calif.) and arterial blood gasses were measured with an IRMA. Blood Analysis system (Diametrics Medical Inc., St. Paul, Minn.). Hemoglobin was measured by a Serno system 9000 (Serno Baker Diagnostics, Allentown, Pa.) preburn and at postburn 6 hours. Animals were euthanatized with sodium pentobarbital (25 mg/kg) and an overdose of a 20% potassium chloride (15–20 m/l) after the final experiment, at postburn 13 hours.

The same regional blood flow technique was used in the ischemia/reperfusion study and in the burn study to measure regional blood flow by the reference sample technique using fluorescent microspheres. Before each measurement, the femoral arterial line was flushed with heparin solution (1000 units/ml, Elkins-Sinn, Inc., Cherry Hill, N.J.) and was connected to a Harvard Apparatus (2400–003, Holliston, Mass.). The latter employed a glass syringe (30 ml) containing heparin (2000 units). Approximately 5 million 15 $\mu$m fluorescent microspheres (Interactive Medical Technology, Los Angeles, Calif.) were injected over 60 seconds through the left arterial catheter, with simultaneous reference blood sample withdrawal by the Harvard Apparatus at 5 ml/min. over 5 minutes. A total of 7 colors were used per animal. After euthanasia a portion of the right renal cortex, exclusive of the juxtamedullary cortex, was excised for the determination of regional blood flow by Interactive Medical Technology (Los Angeles, Calif.) by a flow cytometry technique.

Statistical analysis was performed with Microsoft® Excel (Excel 97, Microsoft, Redmond, Wash.) and SPSS software (SPSS 9.0, SPSS Inc., Chicago, Ill.). A paired T-test was used to compare preburn hemoglobin levels with postburn hour 6 levels. For the other variables, one-way ANOVA with repeated measures on time was used. If the ANOVA was significant, pre-determined post-hoc comparisons in a given variable were made with paired T-tests: each time vs. time 1 (pre burn), time 4 (postburn hour 6) vs. time 1 (preburn), time 5 (resuscitation hour 2) vs. time 4 (postburn hour 6), time 6 (PCWP 16) vs. time 5 (resuscitation hour 2), and time 7 (dobutamine) vs. time 6 (PCWP 16). P values were Bonferroni-corrected for the four non-orthogonal comparisons. A value of $p<0.05$ was considered to indicate a statistically significant result.

Figure 19:
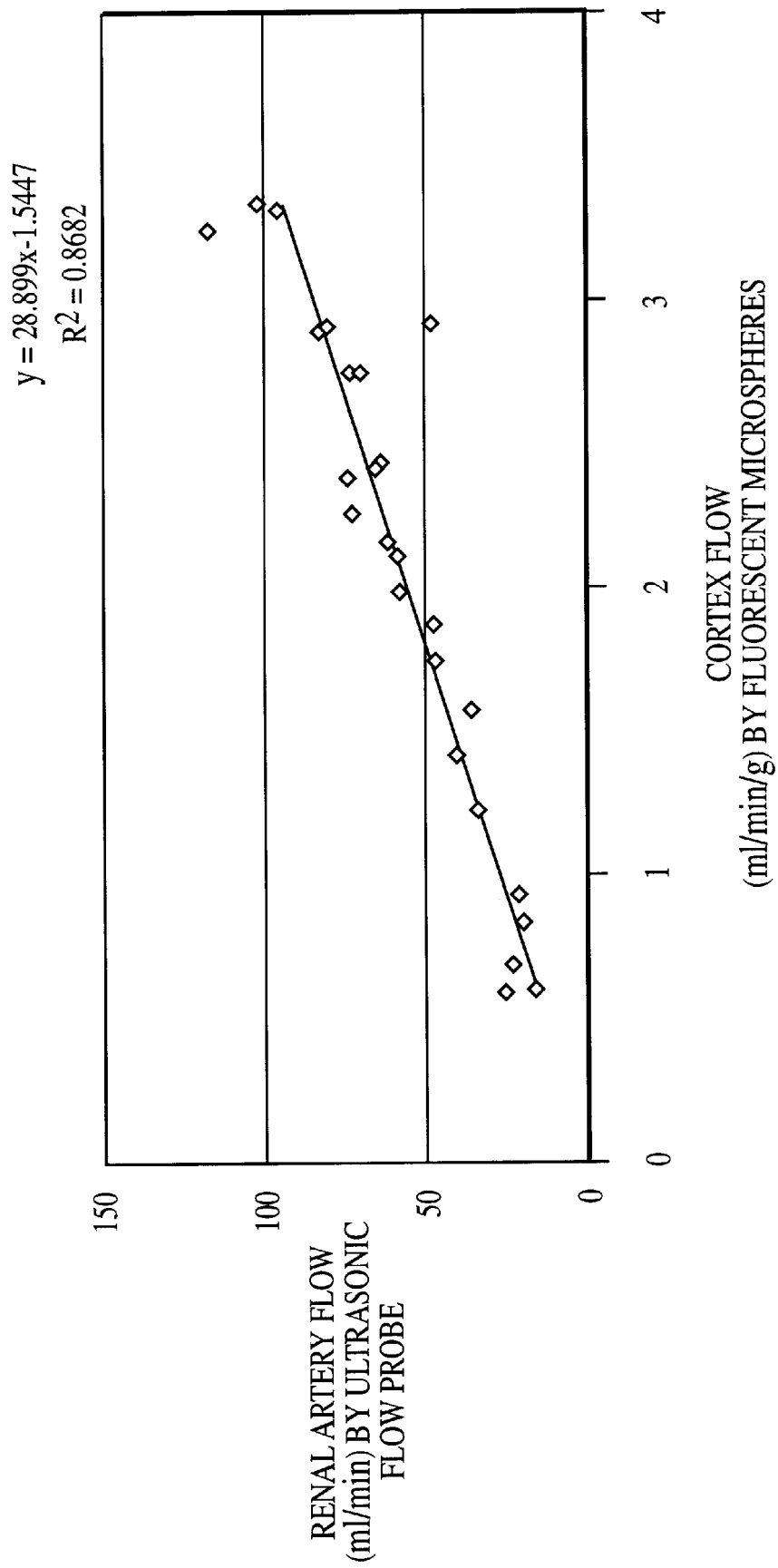
FIG. 19 shows data points illustrating the relationship between renal artery flow and cortex flow.
Figures 20A, 20B:
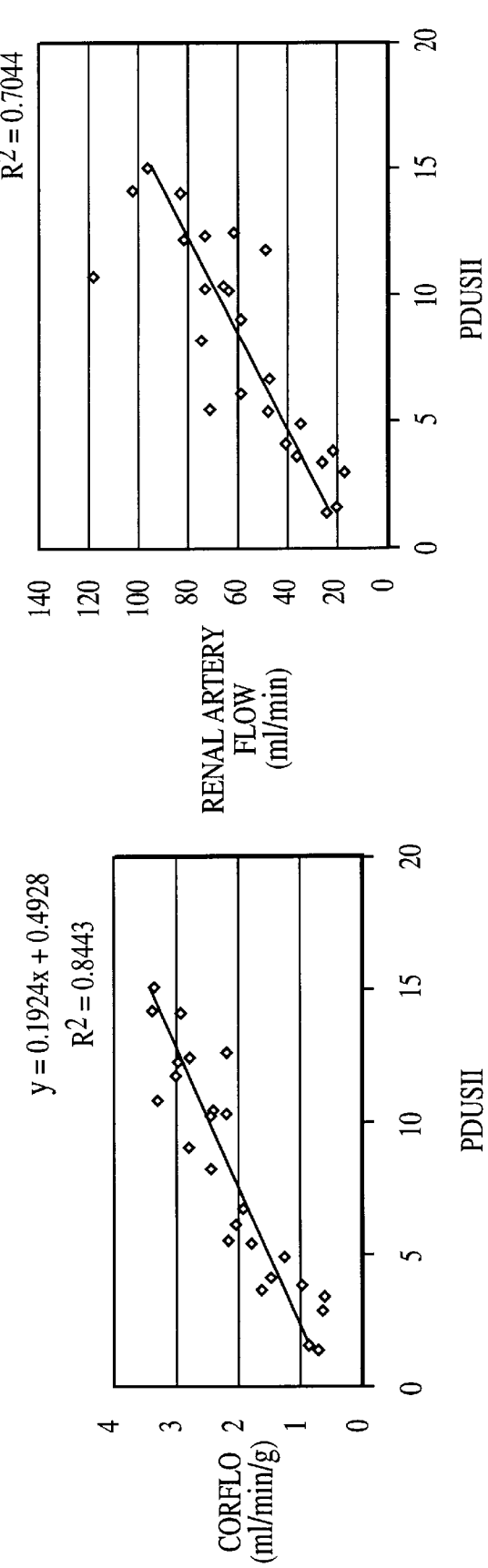
FIG. 20(*a*) shows data points illustrating the relationship between renal cortex blood flow (CORFLO) and power Doppler ultrasound image intensity (PDUSII).

In all of the ischemia/reperfusion study cases, the power Doppler images showed a decrease in qualitative image intensity corresponding to renal artery occlusion and an increase after reperfusion. Renal arterial blood flow measured by flow probe was rectilinearly related to the renal cortex blood flow (CORFLO) determined by fluorescent microspheres (N=25, $r^2$=.868) as shown in FIG. 19. Power Doppler ultrasound image intensity (PDUSII) was also rectilinearly related to the cortical tissue blood flow (N=25, $r^2$=.844) as shown in FIG. 20(a) and arterial blood flow (N=25, $r^2$=.704) as shown in FIG. 20(b).

In the burn size portion of the burn study, the LA50 at 24 hours in the absence of resuscitation was approximately 60% total burn surface area, although the number of animals studied was small and considerable inter-animal variability was observed. No animal died before 4 hours postburn injury.

In 2 out of 3 animals in the burn depth portion of the burn study, the scald burns sustained at 207 F. for 15 seconds produced uniformly full-thickness burns at 24 hours. In the remaining animal deep skin appendages appeared viable, and exposure time for future experiments was therefore prolonged by 13 percent to 17 seconds.

Figure 21:
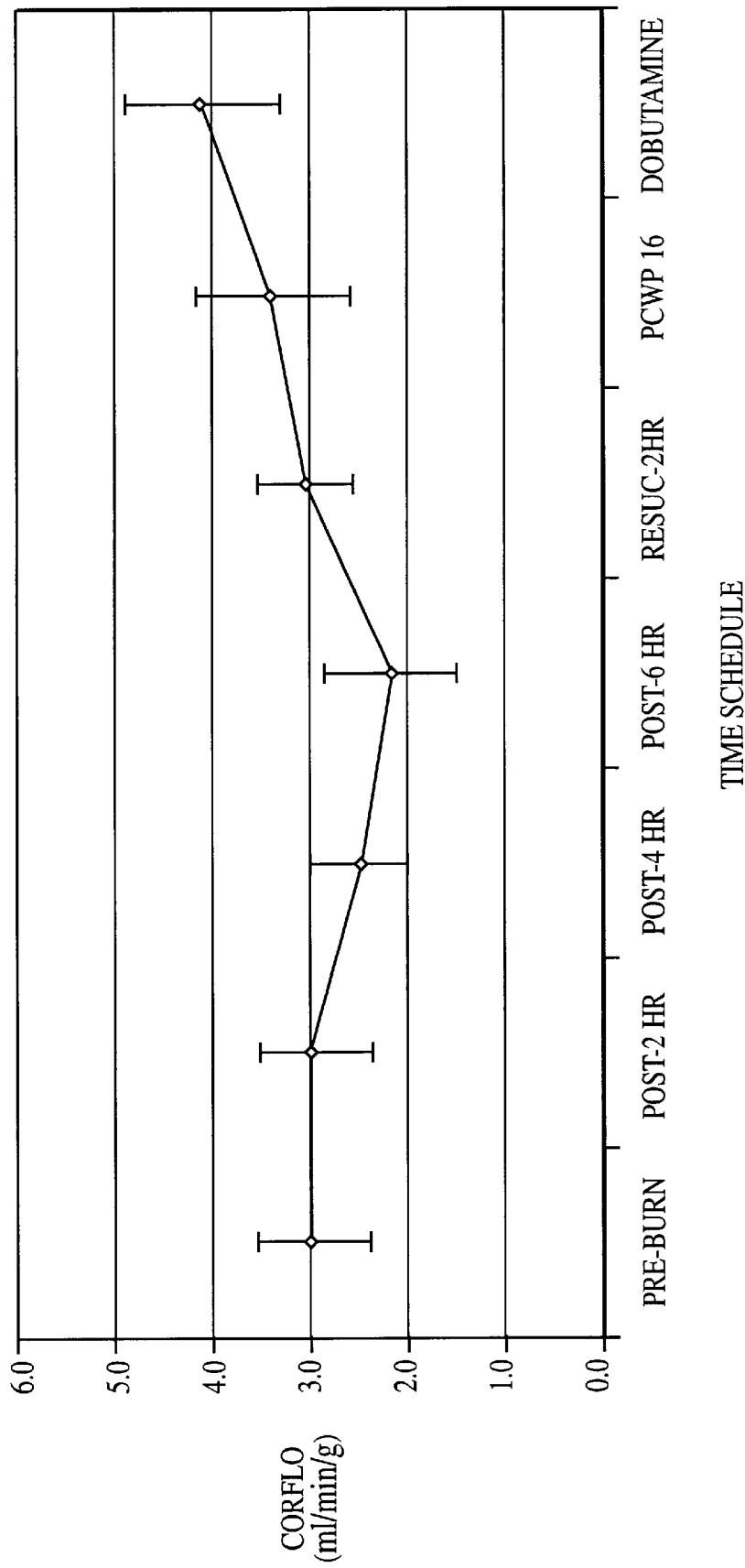
FIG. 21 shows the level of renal cortex blood flow (CORFLO) over time from a point before a burn to a point after the burn.
Figure 22:
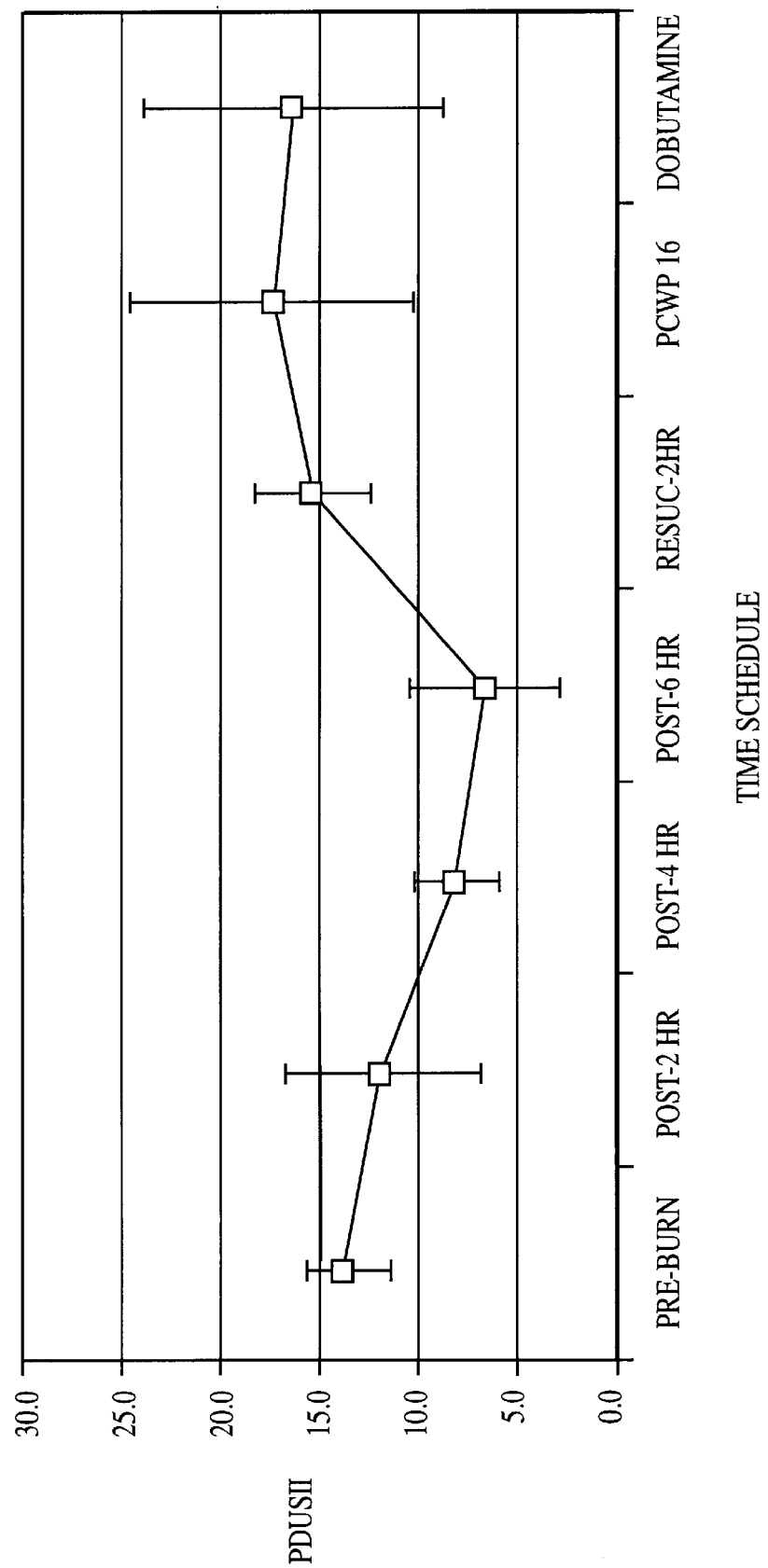
FIG. 22 shows the level of power Doppler ultrasound image intensity (PDUSII) over time from a point before a burn to a point after the burn.
Figure 23:
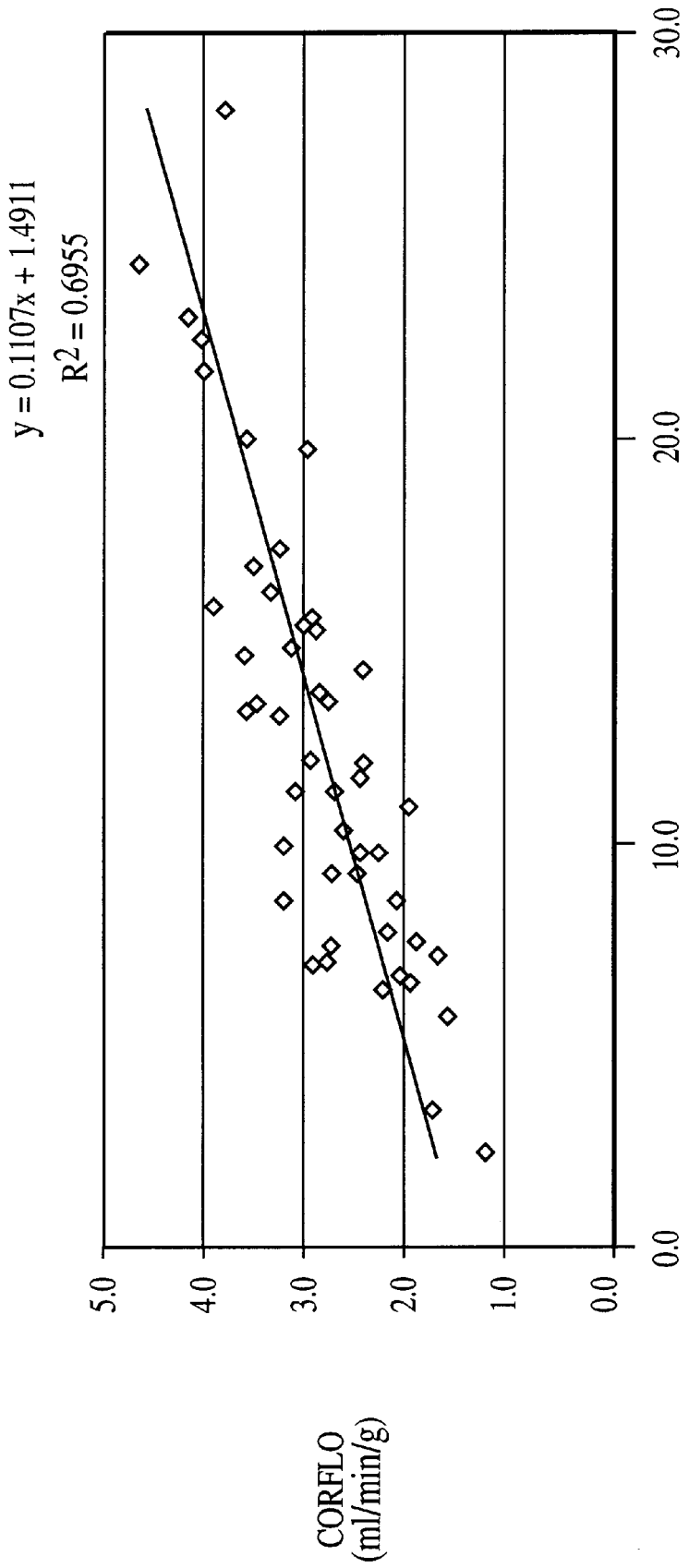
FIG. 23 shows data points illustrating the relationship between renal cortex blood flow (CORFLO) and power Doppler ultrasound image intensity (PDUSII).
Figure 24:
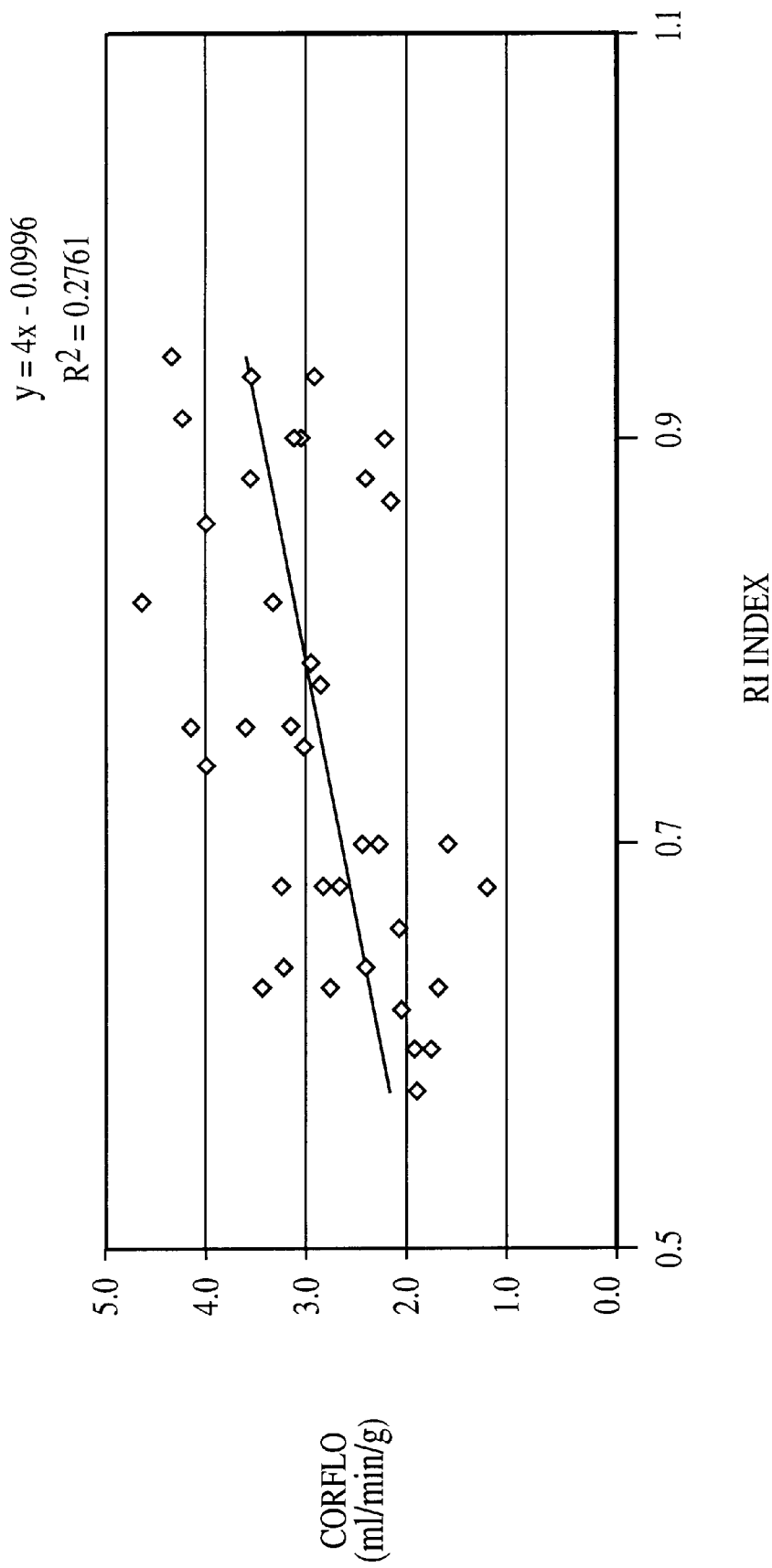
FIG. 24 shows data points illustrating the lack of a relationship between renal cortex blood flow (CORFLO) and of renal artery resistance index (RI Index).
Figure 25:
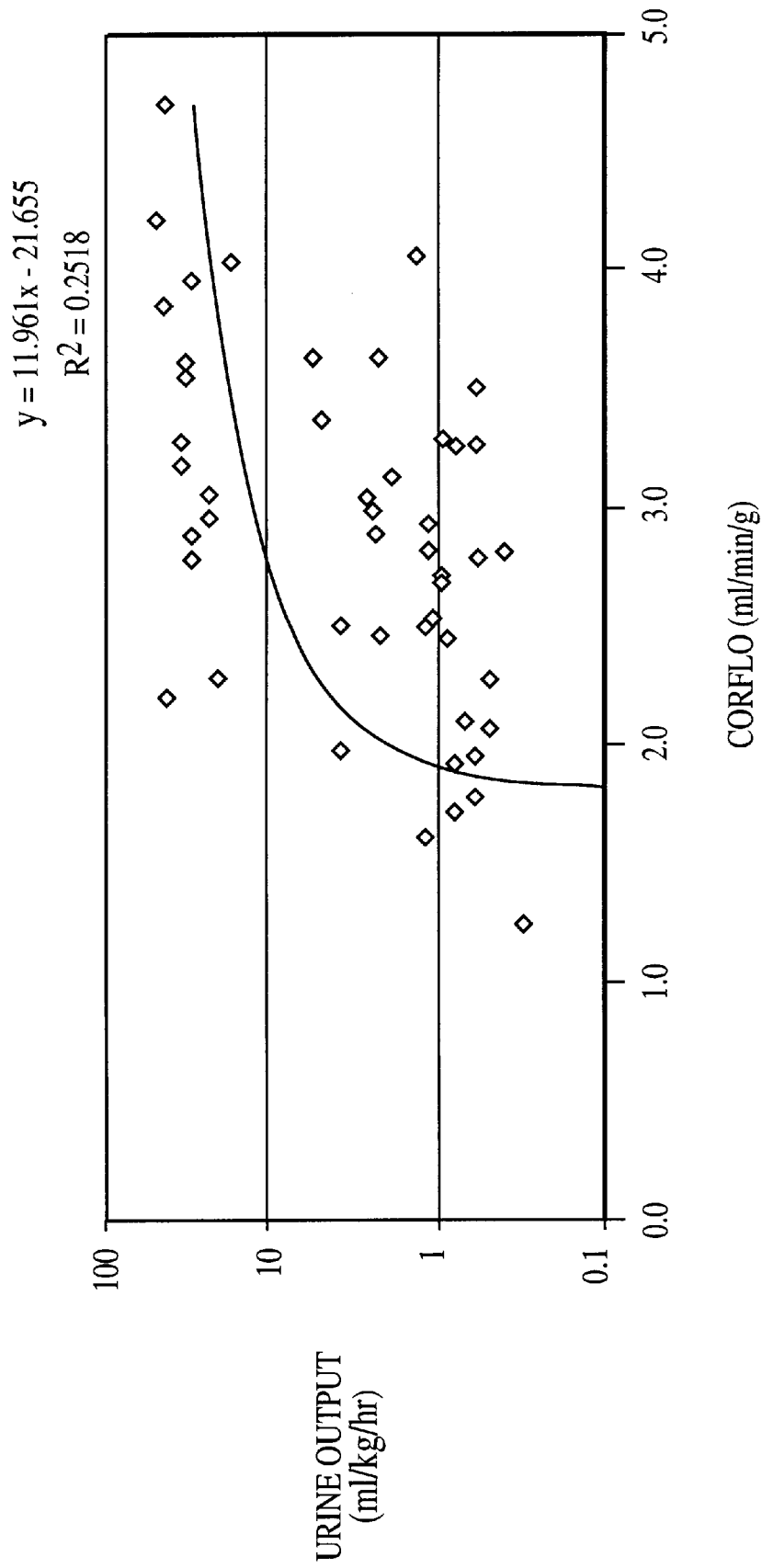
FIG. 25 shows data points illustrating the lack of a relationship between urine output and renal cortex blood flow (CORFLO).

All of the animals in the renal blood flow portion of the burn study lived to completion of the experiment. Typical changes in the renal cortex blood flow (CORFLO) and PDUS images by taking the mean at each measurement time are shown in FIGS. 21 and 22, respectively. The PDUS images consistently showed a decrease in qualitative image intensity during burn shock, and an increase during resuscitation. Renal cortex blood flow (CORFLO) and PDUS image intensity demonstrated similar changes over time as illustrated in FIGS. 21 and 22, respectively. The changes observed in both variables were significantly different between the post-6 hour and resusc-2 hour time points ($p<0.05$). PDUS image intensity showed good correlation with renal cortex blood flow (CORFLO) (n=48, $r^2$=.696) as illustrated in FIG. 23. Renal cortex blood flow (CORFLO) did not correlate with RARTRI (n=38, $r^2$=.276) as illustrated in FIG. 24 or with urine output (n=48, $r^2$=.252) as illustrated in FIG. 25. Cardiac output also correlated well with renal cortex blood flow (CORFLO) (n=48, $r^2$=.611). HR, MPa.P, PCWP, CVP, Cl, SVRI, PH, BE, and urine output changed significantly over time, but Mass.P did not. Cardiac output, central venous pressure, pulmonary capillary wedge pressure and urine output decreased corresponding to time postburn and increased after resuscitation. Conversely, prior to resuscitation systemic vascular resistance (SVR) increased after burn and decreased as resuscitation proceeded. Base excess decreased significantly from 7.86 preburn to 1.69 at the end of the experiment. Hemoglobin increased significantly from 10.0±1.4 mg/dl preburn, to 13.0±2.0 mg/dl at postburn 6 hour (p=0.001).

In conclusion, the study demonstrated that quantified PDUS images of the renal cortex correlated well with cortical tissue blood flow measured by the fluorescent microsphere technique during ischemia/reperfusion and following burn injury.

Those skilled in the art will appreciate that various adaptations and modifications of the above-described preferred embodiments can be configured without departing from the scope and spirit of the invention. Therefore, it is to be understood that, within the scope of the appended claims, the invention may be practiced other than as specifically described herein.

We claim:

1. A method for measuring blood flow through the cortex of a kidney of a patient comprising:

obtaining power Doppler ultrasonogram images of the kidney of the patient, selecting one of the obtained images showing blood flow, selecting a region of interest within the selected image,
performing a histogram of the region of interest, and
calculating an image intensity based on the histogram.

2. The method according to claim 1, wherein said calculating step includes the equation:

$$PDUS \text{ image intensity} = \frac{\sum L_k P_k}{\sum P_k}$$

where $L_k$ is gray-scale level, $P_k$ is number of pixels as a function of gray-scale level, and $\Sigma P_k$ is the total number of pixels within the region of interest.

3. The method according to claim 2, wherein the blood flow through the renal cortex is measured.

4. The method according to claim 1, wherein said obtaining step includes
setting the power Doppler ultrasonographic device to remove the anatomical features of the organ from each image, and
saving each image in a computer readable format.

5. The method according to claim 3, wherein said obtaining step further includes drawing a phantom kidney onto each image.

6. The method according to claim 1, wherein said selecting a region of interest step includes
determining the location of the hilum area of the kidney, and
selecting a portion of the cortex of the kidney opposite the hilum area of the kidney as the region of interest.

7. A system for measuring blood flow through an organ of a patient comprising:
an ultrasound device,
a transducer connected to said ultrasound device,
means for selecting an image received from said ultrasound device,
means for delineating a region of interest within the image,
means for counting the number of pixels at different image gradients within the region of interest,
means for calculating a score based on the number of pixels at different image gradients within the region of interest.

8. The system according to claim 7 wherein said calculating means calculates the score using the following formula $$\text{score} = \frac{\sum L_k P_k}{\sum P_k}$$

where $L_k$ is the gradient level, $P_k$ is number of pixels as a function of gradient level, and $\Sigma P_k$ is the total number of pixels within the region of interest.

9. The system according to claim 8, wherein said ultrasound device includes a power Doppler ultrasound mode.

10. The system according to claim 8, wherein said selecting means includes
a display, and
an user interface for selecting the received image.

11. The system according to claim 8, wherein said ultrasound device includes a drawing interface to mark points of interest in an ultrasound image.

12. The system according to claim 8, wherein said counting means includes a histogram function.

13. The system according to claim 8, further including means for retaining a series of images received from said ultrasound device, said retaining means in communication with said selecting means.

14. The system according to claim 13, further comprising a processing device, said processing device includes said retaining means, said selecting means, said delineating means, said counting means, and said calculating means.

15. The system according to claim 8, wherein said retaining means includes memory.

16. The system according to claim 8, wherein the organ examined is the kidney and the region of interest is the cortex of the kidney opposite the hilum area of the kidney.

17. A method for measuring blood flow through an organ of a patient comprising:
obtaining at least one power Doppler ultrasonogram images of the organ of the patient,
choosing at least one of the obtained images,
selecting a region of interest within said chosen image,
counting the number of pixels at each gradient level within the region of interest, and
calculating a score based on the number of pixels at each gradient level within the region of interest.

18. The method according to claim 12, wherein said calculating the score calculates the score using the following formula $$\text{score} = \frac{\sum L_k P_k}{\sum P_k}$$

where $L_k$ is the number of gradient levels, $P_k$ is number of pixels as a function of gradient level, $\Sigma P_k$ is the total number of pixels within the region of interest, and k is the variable representing each of the gradient levels.

19. A system for analyzing a series of power Doppler ultrasound images of a kidney of a patient and computing a numerical representation of the blood flow through the kidney comprising:
means for selecting an image exhibiting the highest overall blood flow throughout that image,
means for delineating a region outside of the hilum area of the kidney,
means for performing a histogram of the region, and
means for calculating numerical value as follows $$\text{numerical value} = \frac{\sum L_k P_k}{\sum P_k}$$

where $L_k$ is the number of gray-levels possible in the image, $P_k$ is number of pixels as a function of each gray-level possible in the image, $\Sigma P_k$ is the total number of pixels within the region of interest, and k is the variable representing each of the possible gray-levels for that image; and wherein
said performing means produces a series of data for $P_k$ correlated to $L_k$, and
said numerical value represents the amount of blood flow through the kidney.

20. A system for analyzing a series of power Doppler ultrasound images of a kidney of a patient and computing a numerical representation of the blood flow through the kidney comprising:
means for selecting an image exhibiting the highest overall blood flow throughout that image,
means for selecting a region outside of the hilum area of the kidney, means for performing a histogram of the region, and means for calculating a numerical value as follows $$\text{numerical value} = \frac{\sum L_k P_k}{\sum P_k}$$

where $L_k$ is the kth gray-level in the image, $P_k$ is the number of pixels at gray-level $L_k$, $\Sigma P_k$ is the total number of pixels within the region of interest, and k is a number in a range between 1 and the maximum number of gray-levels possible; and wherein said performing means produces a series of data for $P_k$ correlated to $L_k$, and the numerical value represents the amount of blood flow through the kidney.

* * * * *